United States Patent

Schwarz et al.

(10) Patent No.: US 7,635,664 B2
(45) Date of Patent: Dec. 22, 2009

(54) HERBICIDAL SUBSTITUTED BENZOYLPYRAZOLES

(75) Inventors: Hans-Georg Schwarz, Langenfeld (DE); Klaus-Helmut Müller, Düsseldorf (DE); Stefan Herrmann, Langenfeld (DE); Dorothee Hoischen, Düsseldorf (DE); Kristian Kather, Langenfeld (DE); Stefan Lehr, Liederbach (DE); Otto Schallner, Monheim (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 774 days.

(21) Appl. No.: 10/477,800

(22) PCT Filed: May 8, 2002

(86) PCT No.: PCT/EP02/05046

§ 371 (c)(1),
(2), (4) Date: Nov. 14, 2003

(87) PCT Pub. No.: WO02/094792

PCT Pub. Date: Nov. 28, 2002

(65) Prior Publication Data

US 2004/0110640 A1    Jun. 10, 2004

(30) Foreign Application Priority Data

May 21, 2001 (DE) ................... 101 24 578
Aug. 6, 2001 (DE) ................... 101 38 577

(51) Int. Cl.
    A01N 43/56    (2006.01)
    C07D 2331/00  (2006.01)
(52) U.S. Cl. ............. 504/282; 548/366.1; 548/367.4; 548/367.7
(58) Field of Classification Search ........... 504/282; 548/366.1, 367.4, 367.7
See application file for complete search history.

(56) References Cited

U.S. PATENT DOCUMENTS

| | | | | |
|---|---|---|---|---|
| 4,931,565 A | 6/1990 | Baba et al. | .......... | 548/363 |
| 4,986,845 A | 1/1991 | Oya et al. | .......... | 71/92 |
| RE43,779   | 11/1994 | Oya et al. | .......... | 504/282 |
| 5,846,906 A | 12/1998 | von Deyn et al. | .......... | 504/221 |
| 6,124,469 A | 9/2000 | Rheinheimer et al. | .......... | 548/240 |
| 6,156,702 A | 12/2000 | Engel et al. | .......... | 504/282 |
| 6,165,944 A | 12/2000 | von Deyn et al. | .......... | 504/271 |
| 2002/0025910 A1 | 2/2002 | Deyn et al. | .......... | 504/263 |

FOREIGN PATENT DOCUMENTS

| | | |
|---|---|---|
| CA | 2 368 459 | 10/2000 |
| CA | 2 252 543 | 1/2003 |
| EP | 0 177 710 | 4/1986 |
| JP | 11292849 | * 10/1991 |
| JP | 11-292849 | 10/1999 |
| WO | 95/32188 | 11/1995 |
| WO | 97/18196 | 5/1997 |
| WO | 97/46530 | 12/1997 |
| WO | 99/10328 | 3/1999 |

* cited by examiner

*Primary Examiner*—Alton N Pryor
(74) *Attorney, Agent, or Firm*—Richard E. L. Henderson

(57) ABSTRACT

The invention relates to benzoylpyrazoles of the general formula (I),

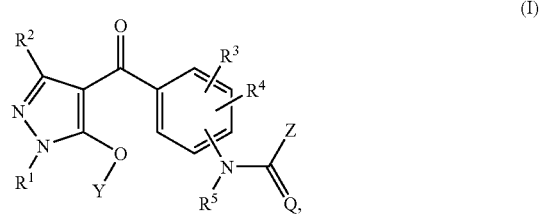

in which Q, $R^1$, $R^2$, $R^3$, $R^4$, $R^5$, Y and Z are as defined in the disclosure, to processes and intermediates for their preparation, and to their use as herbicides.

8 Claims, No Drawings

HERBICIDAL SUBSTITUTED BENZOYLPYRAZOLES

The present patent application has been filed under 35 U.S.C. 371 as a national stage application of PCT/EP02/05046, filed May 8, 2003, which was published in German as International Patent Publication WO 02/094,792 on Nov. 28, 2002, which is entitled to the right of priority of German Patent Applications 101 24 578.5, filed May 21, 2001, and 101 38 577.3, filed Aug. 6, 2001.

The invention relates to novel substituted benzoylpyrazoles, to a process for their preparation and to their use as herbicides.

It is already known that certain substituted benzoylpyrazoles, such as the compounds N-[2,6-dichloro-3-[(5-hydroxy-1-methyl-1H-pyrazol-4-yl)-carbonyl]-phenyl]-acetamide, [2,6-dichloro-3-[(5-hydroxy-1-methyl-1H-pyrazol-4-yl)-carbonyl]-phenyl]-carbamic acid methyl ester, N'-[2,6-dichloro-3-[(5-hydroxy-1-methyl-1H-pyrazol-4-yl)-carbonyl]-phenyl]-N,N-diethyl-urea, [2-chloro-3-[(5-hydroxy-1-methyl-1H-pyrazol-4-yl)-carbonyl]-6-methylsulphonyl-phenyl]-carbamic acid methyl ester, N'-[2-chloro-3-[(5-hydroxy- 1-methyl-1H-pyrazol-4-yl)-carbonyl]-6-methylsulphonyl-phenyl]-N,N-diethyl-urea, N-[3-[(1-ethyl-5-hydroxy- 1H-pyrazol-4-yl)-carbonyl]-2-methyl-6-methylsulphonyl-phenyl]-acetamide, N-[3-[(5-hydroxy- 1-methyl- 1H-pyrazol-4-yl)-carbonyl]-2-methyl-6-methylsulphonyl-phenyl]-propanamide, N-[3-[(5-hydroxy-1-methyl-1H-pyrazol-4-yl)-carbonyl]-2-methyl-6-methylsulphonyl-phenyl]-acetamide, N'-[2-chloro-3-[( 1-ethyl-5-hydroxy-1H-pyrazol-4-yl)-carbonyl]-6-methyl-sulphonyl-phenyl]-N,N-diethyl-urea, N-[3-[(5-hydroxy-1-methyl-1H-pyrazol-4-yl)-carbonyl]-2-methyl-6-methylsulphonyl-phenyl]-formamide, [3-[(5-hydroxy-1-methyl-1H-pyrazol-4-yl)-carbonyl]-2-methyl-6-methylsulphonyl-phenyl]-carbamic acid methyl ester, N-[2-chloro-3-[(1-ethyl-5-hydroxy-1H-pyrazol-4-yl)-carbonyl]-6-methylsulphonyl-phenyl]-acetamide, N-[2-chloro-3-[(5-hydroxy-1-methyl-1H-pyrazol-4-yl)-carbonyl]-6-methylsulphonyl-phenyl]-acetamide, N-[3-[(5-hydroxy- 1-methyl-1H-pyrazol-4-yl)-carbonyl]-2-methyl-6-methylsulphonyl-phenyl]-2,2,2-trifluoro-acetamide, N-[3-[(1-ethyl-5-hydroxy-1H-pyrazol-4-yl)-carbonyl]-2-methyl-6-methylsulphonyl-phenyl]-2,2,2-trifluoro-acetamide, N-[3-[(5-Hydroxy-1-methyl-1H-pyrazol-4-yl)-carbonyl]-2-methyl-6-methylsulphonyl-phenyl]-N-methyl-formamide, N-[2-chloro-3-[(5-hydroxy-1-methyl-1H-pyrazol-4-yl)-carbonyl]-6-methylsulphonyl-phenyl]-N-methyl-carbamic acid methyl ester, N-[2-chloro-3-[(5-hydroxy-1-methyl-1H-pyrazol-4-yl)-carbonyl]-6-methylsulphonyl-phenyl]-N,N'-di ethyl-N-methyl-urea and N-[2,6-dichloro-3-[(5-hydroxy-1-methyl-1H-pyrazol-4-yl)-carbonyl]-phenyl]-N-methyl-carbamic acid methyl ester (cf. JP-A-11292849—cited in Chem. Abstracts 131:286507) have herbicidal properties (cf. also EP-A-352543, U.S. Pat. No. 5,846,907, WO-A-96/26206, WO-A-97/41105, WO-A-97/41116, WO-A-97/41117, WO-A-97/41118, WO-A-97/46530, WO-A-98/28981, WO-A-98/31681, WO-A-98/31682, WO-A-99/07697, WO-A-99/10328, WO-A-00/58306). However, the activity of these compounds is not entirely satisfactory.

This invention, accordingly, provides the novel substituted benzoylpyrazoles of the general formula (I)

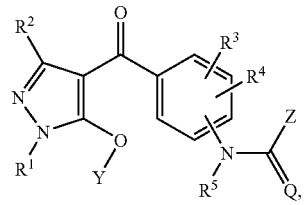

(I)

in which

Q represents O (oxygen) or S (sulphur), $R^1$ represents in each case optionally substituted alkyl, alkenyl, alkinyl or cycloalkyl, $R^2$ represents hydrogen, cyano, carbamoyl, thiocarbamoyl, halogen, or represents in each case optionally substituted alkyl, alkoxy, alkylthio, alkoxycarbonyl or cycloalkyl, $R^3$, $R^4$ independently of one another represent hydrogen, nitro, cyano, carboxyl, carbamoyl, thiocarbamoyl, halogen, or in each case optionally substituted alkyl, alkoxy, alkylthio, alkylsulphinyl, alkylsulphonyl, alkylamino, dialkylamino, dialkylaminocarbonyl or dialkylaminosulphonyl, $R^5$ represents hydrogen or represents in each case optionally substituted alkyl, alkoxy, alkylthio, alkylsulphinyl, alkylsulphonyl, alkenyl, alkinyl, cycloalkyl, cycloalkylalkyl, aryl, arylthio, arylsulphinyl, arylsulphonyl, arylalkyl, or represents the grouping —C(Q)-Z, Y represents hydrogen or in each case optionally substituted alkyl, alkylsulphonyl, alkylcarbonyl, alkoxycarbonyl, alkylaminocarbonyl, dialkylaminocarbonyl, alkenyl, alkenylsulphonyl, alkenylcarbonyl, alkinyl, alkinylcarbonyl, cycloalkyl, cycloalkylcarbonyl, cycloalkylalkyl, phenyl, phenylsulphonyl, phenylcarbonyl, phenylalkyl, phenylalkylsulphonyl, phenylalkylcarbonyl or phenylcarbonylalkyl, and Z represents amino, cyanoamino, nitroamino, hydroxyamino, hydrazino, represents in each case cyano-, alkoxy-, alkylthio-, alkylsulphinyl- or alkylsulphonyl-substituted alkyl, alkoxy, alkylthio or alkylamino, represents in each case optionally substituted alkylcarbonyl, alkoxycarbonyl, alkoxyamino, alkylhydrazino, alkylcarbonylhydrazino, alkoxycarbonylhydrazino, alkylsulphonylhydrazino, N-alkyl-alkoxyamino, dialkylhydrazino, alkenyloxy, alkenylamino, alkenyloxyamino, aLkinyloxy, alkinylamino, cycloalkyl, cycloalkyloxy, cycloalkylamino, cycloalkylhydrazino, cycloalkylalkyl, cycloalkylalkoxy, cycloalkylalkylamino, aryl, arylcarbonyl, aryloxy, aryloxycarbonyl, arylthio, arylamino, arylhydrazino, arylalkyl, arylalkoxy, arylalkylthio, arylalkylamino, heterocyclyl, heterocyclyloxy, heterocyclylthio, heterocyclylamino, the grouping —N=(heterocyclyl), heterocyclylalkyl, heterocyclylalkoxy, heterocyclylalkylthio or heterocyclylalkylamino, including all possible tautomeric forms of the compounds of the general formula (I) and the possible salts of the compounds of the general formula (I).

Preferred meanings of the radicals or groupings present in the formulae given above and below are defined below.

Q preferably represents O.

$R^1$ preferably represents optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl- substituted alkyl having 1 to 6 carbon atoms, represents in each case optionally cyano- or halogen-substituted alkenyl or alkinyl having in each case 2 to 6 carbon atoms, or represents optionally cyano-, halogen- or $C_1$-$C_4$-alkyl-substituted cycloalkyl having 3 to 6 carbon atoms.

$R^2$ preferably represents hydrogen, cyano, carbamoyl, thiocarbamoyl, halogen, represents in each case optionally cyano-, halogen- or $C_1$-$C_4$-alkoxy-substituted alkyl, alkoxy or alkoxycarbonyl having in each case up to 6 carbon atoms, represents optionally halogen-substituted alkylthio having 1 to 6 carbon atoms, or represents optionally cyano-, halogen- or $C_1$-$C_4$-alkyl-substituted cycloalkyl having 3 to 6 carbon atoms.

$R^3$, $R^4$ independently of one another preferably represent hydrogen, nitro, cyano, carboxyl, carbamoyl, thiocarbamoyl, halogen, represent in each case optionally halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl or alkylsulphonyl having in each case up to 4 carbon atoms in the alkyl groups, or represent alkylamino, dialkylamino, dialkylaminocarbonyl or dialkylaminosulphonyl having in each case up to 4 carbon atoms in the alkyl groups.

$R^5$ preferably represents hydrogen, represents in each case optionally cyano-, halogen- or $C_1$-$C_4$-alkoxy-substituted alkyl, alkoxy, alkylthio, alkylsulphinyl, alkylsulphonyl having in each case 1 to 6 carbon atoms in the alkyl groups, represents in each case optionally cyano- or halogen-substituted alkenyl or alkinyl having in each case 3 to 6 carbon atoms in the alkenyl and alkinyl groups, respectively, represents in each case optionally cyano-, halogen- or $C_1$-$C_4$-alkyl-substituted cycloalkyl or cycloalkylalkyl having in each case 3 to 6 carbon atoms in the cycloalkyl groups and, if appropriate, 1 to 4 carbon atoms in the alkyl moiety, represents in each case optionally nitro- cyano-, $C_1$-$C_4$-alkyl-, $C_1$-$C_4$-halogenalkyl-, $C_1$-$C_4$-alkoxy-, $C_1$-$C_4$-halogenalkoxy-, $C_1$-$C_4$-alkylthio-, $C_1$-$C_4$-halogenalkylthio-, $C_1$-$C_4$-alkylsulphinyl-, $C_1$-$C_4$-halogenalkylsulphinyl-, $C_1$-$C_4$-alkylsulphonyl- or $C_1$-$C_4$-halogenalkyl-sulphonyl-substituted aryl, arylthio, arylsulphinyl, arylsulphonyl or arylalkyl having in each case 6 or 10 carbon atoms in the aryl groups and, if appropriate, 1 to 4 carbon atoms in the alkyl moiety, or represents the grouping —C(Q)-Z.

Y preferably represents hydrogen, represents optionally cyano-, carbamoyl-, halogen-, $C_1$-$C_4$-alkoxy- or $C_1$-$C_4$-alkoxy-carbonyl-substituted alkyl having 1 to 6 carbon atoms, represents optionally halogen-substituted alkylsulphonyl having 1 to 6 carbon atoms, represents in each case optionally cyano-, halogen- or $C_1$-$C_4$-alkoxy-substituted alkylcarbonyl, alkoxycarbonyl or alkylaminocarbonyl having in each case 1 to 6 carbon atoms in the alkyl groups, represents dialkylaminocarbonyl having 1 to 4 carbon atoms in the alkyl groups, represents in each case optionally cyano- or halogen-substituted alkenyl, alkenylcarbonyl, alkinyl or alkinylcarbonyl having in each case up to 6 carbon atoms, represents optionally halogen-substituted alkenylsulphonyl having up to 6 carbon atoms, represents in each case optionally cyano-, halogen- or $C_1$-$C_4$-alkyl-substituted cycloalkyl, cycloalkylcarbonyl or cycloalkylalkyl having in each case 3 to 6 carbon atoms in the cycloalkyl groups and, if appropriate, 1 to 3 carbon atoms in the alkyl moiety, or represents in each case optionally nitro-, cyano-, carbamoyl-, halogen-, $C_1$-$C_4$-alkyl-, $C_1$-$C_4$-halogenalkyl-, $C_1$-$C_4$-alkoxy- or $C_1$-$C_4$-halogenalkoxy-substituted phenyl, phenylsulphonyl, phenylcarbonyl, phenyl-$C_1$-$C_4$-alkyl, phenyl-$C_1$-$C_4$-alkyl-sulphonyl, phenyl-$C_1$-$C_4$-alkyl-carbonyl or phenylcarbonyl-$C_1$-$C_4$-alkyl.

Z preferably represents amino, cyanoamino, nitroamino, hydroxyamino, hydrazino, represents in each case cyano-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio or alkylamino having in each case 1 to 6 carbon atoms, represents $C_1$-$C_4$-alkylcarbonyl or $C_1$-$C_4$-alkoxycarbonyl, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxyamino, alkylhydrazino, alkylcarbonylhydrazino, alkoxycarbonylhydrazino or alkylsulphonylhydrazino having in each case 1 to 6 carbon atoms in the alkyl groups, represents N-alkyl-alkoxyamino or dialkylhydrazino having in each case 1 to 4 carbon atoms in the alkyl groups, represents in each case optionally halogen-substituted alkenyloxy, alkenylamino, alkenyloxyamino, alkinyloxy or alkinylamino having in each case 2 to 6 carbon atoms, represents in each case optionally cyano-, halogen- or $C_1$-$C_4$-alkyl-substituted cycloalkyl, cycloalkyloxy, cycloalkylamino, cycloalkylhydrazino, cycloalkylalkyl, cycloalkylalkoxy or cycloalkylalkylamino having in each case 3 to 6 carbon atoms in the cycloalkyl group and, if appropriate, 1 to 4 carbon atoms in the alkyl moiety, represents in each case optionally nitro-, cyano-, halogen-, $C_1$-$C_4$-alkyl-, $C_3$-$C_6$-cycloalkyl-, $C_1$-$C_4$-halogenalkyl-, $C_1$-$C_4$-alkoxy-, $C_1$-$C_4$-halogenalkoxy- or $C_1$-$C_4$-alkoxy-carbonyl-substituted aryl, arylcarbonyl, aryloxy, aryloxycarbonyl, arylthio, arylamino, arylhydrazino, arylalkyl, arylalkoxy, arylalkylthio or arylalkylamino having in each case 6 or 10 carbon atoms in the aryl group and, if appropriate, 1 to 4 carbon atoms in the alkyl moiety, or represents in each case optionally nitro-, cyano-, halogen-, $C_1$-$C_4$-alkyl-, $C_3$-$C_6$-cycloalkyl-, $C_1$-$C_4$-halogenalkyl-, $C_1$-$C_4$-alkoxy-, $C_1$-$C_4$-halogenalkoxy-, $C_1$-$C_4$-alkylthio-, $C_1$-$C_4$-halogenalkylthio- or $C_1$-$C_4$-alkoxycarbonyl-substituted monocyclic or bicyclic heterocyclyl, heterocyclyloxy, heterocyclylthio, heterocyclylamino, the grouping —N=(heterocyclyl), heterocyclylalkyl, heterocyclylalkoxy, heterocyclylalkylthio or heterocyclylalkylamino where in each case the heterocyclyl grouping contains up to 10 carbon atoms and additionally at least one heteroatom selected from the group consisting of nitrogen (but at most 5 N atoms), oxygen (but at most 2 O atoms), sulphur (but at most 2 S atoms), SO or $SO_2$ and, if appropriate, additionally one group selected from the group consisting of oxo (C=O), thioxo (C=S), imino (C=NH), cyanoimino (C=N—CN), nitroimino (C=N—$NO_2$) and where, if appropriate, the alkyl moiety contains 1 to 4 carbon atoms.

$R^1$ particularly preferably represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, ethyl, n- or i-propyl, n-, i-, s- or, t-butyl, represents in each case optionally cyano-, fluorine-, chlorine- or bromine-substituted propenyl, butenyl, propinyl or butinyl, or represents in each case optionally cyano-, fluorine-, chlorine-, bromine-, methyl- or ethyl-substituted cyclopropyl, cyclobutyl, cyclopentyl or cyclohexyl.

$R^2$ particularly preferably represents hydrogen, cyano, carbamoyl, thiocarbamoyl, fluorine, chlorine, bromine, represents in each case optionally cyano-, fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, represents in each case optionally fluorine- and/or chlorine-substituted methylthio, ethylthio, n- or i-propylthio, or represents in each case optionally cyano-, fluorine-, chlorine-, bromine-methyl- or ethyl-substituted cyclopropyl, cyclobutyl, cyclopentyl or cyclohexyl.

$R^3$, $R^4$ independently of one another particularly preferably represent hydrogen, nitro, cyano, carboxyl, carbamoyl, thiocarbamoyl, fluorine, chlorine, bromine, iodine, represent in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represent methylamino, ethylamino, n- or i-propylamino, n-, i-, s- or t-butylamino, dimethylamino, diethylamino, dimethylaminocarbonyl, diethylaminocarbonyl, dimethylaminosulphonyl or diethylaminosulphonyl.

$R^5$ particularly preferably represents hydrogen, represents in each case optionally-cyano-, fluorine-, chlorine-, bromine-, methoxy-, ethoxy-, n- or i-propoxy-substituted methyl, ethyl, n- or i-propyl, n-, i-, s- or t-butyl, n-, i-, s-, or t-pentyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, methylamino, ethylamino, n- or i-propylamino, n-, i-, s- or t-butylamino, represents dimethylamino or diethylamino, represents in each case optionally fluorine-, chlorine- and/or bromine-substituted ethenyl, propenyl, butenyl, pentenyl, ethinyl, propinyl, butinyl or pentinyl, represents in each case optionally cyano-, fluorine-, chlorine-, bromine-, methyl- orethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl, n-, i-, s- or t-butyl-, trifluoromethyl-, methoxy-, ethoxy-, n- or i-propoxy-, difluoromethoxy- or trifluoromethoxy-substituted phenyl, phenylthio, phenylsulphinyl, phenylsulphonyl, naphthyl, phenylnethyl, phenylethyl, naphthylmethyl or naphthylethyl or represents the grouping —C(Q)-Z.

Y particularly preferably represents hydrogen, represents in each case optionally cyano-, carbamoyl-, fluorine-, chlorine-, methoxy-, ethoxy-, n- or i-propoxy-, methoxycarbonyl-, ethoxycarbonyl-, n- or i-propoxycarbonyl-substituted methyl, ethyl, n- or i-propyl, represents in each case optionally fluorine- and/or chlorine-substituted methylsulphonyl, ethylsulphonyl, n- or i-propylsulphonyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, represents dimethylaminocarbonyl or diethylaminocarbonyl, represents in each case optionally cyano-, fluorine-, chlorine- or bromine-substituted propenyl, butenyl, propenylcarbonyl, butenylcarbonyl, propinyl, butinyl, propinylcarbonyl or butinylcarbonyl, represents in each case optionally fluorine- and/or chlorine-substituted propenylsulphonyl or butenylsulphonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropylmethyl, cyclobutylmethyl, cyclopentylmethyl or cyclohexylmethyl, or represents in each case optionally nitro-, cyano-, carbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylsulphonyl, phenylcarbonyl, phenylmethyl, phenylethyl, phenylmethylsulphonyl, phenylmethylcarbonyl or phenylcarbonylmethyl.

Z particularly preferably represents amino, cyanoamino, nitroamino, hydroxyamino, hydrazino, represents in each case cyano-, methoxy-, ethoxy-, n- or i-propoxy-, methylthio-, ethylthio-, n- or i-propylthio-, methylsulphinyl, ethylsulphinyl, n- or i-propylsulphinyl, methylsulphonyl or ethylsulphonyl-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methoxyamino, ethoxyamino, n- or i-propoxyamino, n-, i-, s- or t-butoxyamino, methylhydrazino, ethylhydrazino, n- or i-propylhydrazino, n-, i-, s- or t-butylhydrazino, represents N-methylmethoxyamino or dimethylhydrazino, represents in each case optionally fluorine-, chlorine- and/or bromine-substituted propenyloxy, butenyloxy, pentenyloxy, propenylthio, butenylthio, pentenylthio, propenylamino, butenylamino, pentenylamino, propenyloxyamino, butenyloxyamino, pentenyloxyamino, propinyloxy, butinyloxy, pentinyloxy, propinylamino, butinylamino or pentinylamino, represents in each case optionally cyano-, fluorine-, chlorine-, bromine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylhydrazino, cyclobutylhydrazino, cyclopentylhydrazino, cyclohexylhydrazino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, naphthyl, naphthyloxy, naphthylthio, naphthylamino, phenylmethyl, phenylethyl, phenylmethoxy, phenylethoxy, phenylmethylthio, phenylethylthio, phenylmethylamino, phenylethylamino, naphthylmethyl, naphthylethyl, naphthylmethoxy, naphthylethoxy, naphthylmethylamino or naphthylethylamino, or represents in each case optionally nitro-, cyano-, fluorine-, chlorine- bromine-, methyl-, ethyl-, n- or i-propyl-, n-, i-, s- or t-butyl-, cyclopropyl-, cyclobutyl-, cyclopentyl-, cyclohexyl-, difluoromethyl-, trifluormethyl-, dichloromethyl-, trichloromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio, methoxycarbonyl-, ethoxycarbonyl-, n- or i-propoxycarbonyl-substituted monocyclic or bicyclic heterocyclyl, heterocyclyloxy, heterocyclylamino, the grouping —N=(heterocyclyl), heterocyclylalkyl, heterocyclylalkoxy or heterocyclylalkylamino from the group consisting of furyl, furyloxy, furylamino, furylmethyl, furylmethoxy, furylmethylamino, tetrahydrofuryl, tetrahydrofuryloxy, tetrahydrofurylamino, tetrathydrofurylmethyl, tetrahydrofurylmethoxy, tetrahydrofurylmethylamino, dioxolanyl, dioxolanylmethyl, dioxolanylmethoxy, dioxolanylmethylamino, thienyl, thienylamino, thienylmethyl, thienylmethylamino, dithiolanyl, dithiolanylmethyl, dithiolanylmethoxy, dithiolanylmethylamino, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, iimidazolinylmethyl, oxoimidazolinyl, 2-oxo-1,3-diaza-cyclopentyl, oxazolyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), tetrahydro-(2H)-1,2-oxazin-2-yl, oxazolylmethyl, thiazolyl, dihydrothiazolyl (thiazolinyl), tetrahydrothiazolyl (thiazolidinyl), thiazolimino, thiazolylmethyl, dihydrothiazolyl (thiazolinyl), tetrahydrothiazolyl (thiazolidinyl), oxothiazolidinyl, cyanoiminothiazolidinyl, oxadiazolylamino, thiadiazolylamino, oxotriazolinyl, oxotetrazolinyl, dioxanyl, dioxanylmethyl, dioxanylmethoxy, dioxanylmethylamino, dithianyl, dithianylmethyl, dithianylmethoxy, dithianylmethylamino, triazolylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, oxomorpholinyl, morpholinylamino, piperazinyl, pyridinyl, pyridinyloxy, pyridinylamino, 2-(1H)-pyridinimino, pyridinylmethyl, pyridinylmethoxy, pyrimidinyl, pyrimidinyloxy, pyrimidinylmethyl or pyrimidinylmethoxy.

$R^1$ very particularly preferably represents methyl, ethyl, n- or i-propyl, cyclopropyl, cyclopentyl or cyclohexyl.

$R^2$ very particularly preferably represents hydrogen, represents in each case optionally fluorine-, chlorine-, methoxy- or ethoxy-substituted methyl, ethyl, methoxycarbonyl or ethoxycarbonyl, represents in each case optionally fluorine- and/or chlorine-substituted methylthio or ethylthio, or represents optionally fluorine-, chlorine- or methyl-substituted cyclopropyl.

$R^3$, $R^4$ independently of one another very particularly preferably represent hydrogen, nitro, cyano, fluorine, chlorine, bromine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^5$ very particularly preferably represents hydrogen, represents in each case optionally cyano-, fluorine-, chlorine-, methoxy- or ethoxy-substituted methyl, ethyl, n- or i-propyl, n- or i-butyl, represents methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, methylamino, ethylamino, n- or i-propylamino or dimethylamino, represents in each case optionally fluorine- and/or chlorine-substituted propenyl, butenyl, propinyl or butinyl, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl, n-, i-, s- or t-butyl-, trifluoromethyl-, methoxy-, ethoxy-, n- or i-propoxy-, difluoromethoxy- or trifluoromethoxy-substituted phenyl, phenylthio, phenylsulphinyl, phenylsulphonyl, phenylmethyl or phenylethyl, or represents the grouping —C(Q)-Z.

Y very particularly preferably represents hydrogen, represents in each case optionally cyano-, fluorine-, methoxy-, ethoxy-, methoxycarbonyl- or ethoxycarbonyl-substituted methyl or ethyl, represents in each case optionally fluorine- and/or chlorine-substituted methylsulphonyl or ethylsulphonyl, represents in each case optionally cyano-, fluorine-, chlorine-, methoxy- or ethoxy-substituted acetyl, propionyl, methoxycarbonyl, ethoxycarbonyl, methylaminocarbonyl or ethylaminocarbonyl, represents dimethylaminocarbonyl, represents in each case optionally fluorine-, chlorine- or bromine-substituted propenyl, propenylcarbonyl, propinyl or propinylcarbonyl, represents in each case optionally cyano-, fluorine-, chlorine- or methyl-substituted cyclopropylcarbonyl, cyclobutylcarbonyl, cyclopentylcarbonyl, cyclohexylcarbonyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, trifluoromethyl-, methoxy-, ethoxy-, difluoromethoxy- or trifluoromethoxy-substituted phenyl, phenylsulphonyl, phenylcarbonyl, phenylmethyl, phenylmethylsulphonyl, phenylmethylcarbonyl or phenylcarbonylmethyl.

Z very particularly preferably represents amino, cyanoamino, hydrazino, represents in each case optionally cyano-, methoxy-, ethoxy-, n- or i-propoxy-, methylthio-, ethylthio-, n- or i-propylthio-, methylsulphinyl, ethylsulphinyl, n- or i-propylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylamino, ethylamino, n- or i-propylamino, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methoxyamino, ethoxyamino, n- or i-propoxyamino, methylhydrazino-, ethylhydrazino-, n- or i-propylhydrazino, n-, i-, s- or t-butylhydrazino, N-methyl-methoxyamino or dimethylhydrazino, represents in each case optionally fluorine- and/or chlorine-substituted propenyloxy, butenyloxy, propenylthio, butenylthio, propenylamino, butenylamino, propenyloxyamino, butenyloxyamino, propinyloxy, butinyloxy, propinylamino or butinylamino, represents in each case optionally cyano-, fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopentylhydrazino, cyclohexylhydrazino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-; ethoxycarbonyl-, n- or i-propoxycarbonyl-substituted phenyl, phenylcarbonyl, phenoxy, phenoxycarbonyl, phenylthio, phenylamino, phenylhydrazino, phenylmethyl, phenylethyl, phenylmethoxy, phenylethoxy, phenylmethylthio, phenylethylthio, phenylmethylamino or phenylethylamino, or represents in each case optionally nitro-, cyano-, fluorine-, chlorine-, bromine-, methyl-, ethyl-, n- or i-propyl, n-, i-, s- or t-butyl-, cyclohexyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, the grouping —N=(heterocyclyl), heterocyclylalkyl, heterocyclylalkoxy or heterocyclylalkylamino from the group consisting of furyl, furyloxy, furylamino, furylmethyl, furylmethoxy, furylmethylamino, tetrahydrofuryl, tetrahydrofuryloxy, tetrahydrofurylamino, tetrahydrofurylmethyl, tetrahydrofurylmethoxy, tetrahydrofurylmethylamino, dioxolanyl, dioxolanylmethyl, dioxolanylmethoxy, dioxolanylmethylamino, thienyl, thienylamino, thienylmethyl, thienylmethylamino, dithiolanyl, dithiolanylmethyl, dithiolanylmethoxy, dithiolanylmethylamino, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, imidazolinylmethyl, 2-oxo-1,3-diaza-cyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), tetra-hydro-(2H)-1,2-oxazin-2-yl, thiazolyl, thiazolylmethyl, dihydrothiazolyl (thiazolinyl), tetrahydrothiazolyl (thiazolidinyl), thiazolimino, oxothiazolidinyl, cyanoiminothiazolidinyl, oxadiazolylamino, thiadiazolylamino, oxotriazolinyl, oxotetrazolinyl, dioxanyl, dioxanylmethyl, dioxanylmethoxy, dioxanylmethylamino, dithianyl, dithianylmethyl, dithianylmethoxy, dithianylmethylamino, triazolylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, oxo-morpholinyl, morpholinylamino, piperazinyl, pyridinyl, pyridinyloxy, pyridinylamino, 2-(1H)-pyridinimino, pyridinylmethyl, pyridinylmethoxy, pyrimidinyl, pyrimidinyloxy, pyrimidinylmethyl or pyrimidinylmethoxy.

A very particularly preferred group are those compounds of the general formula (I) in which Q represents O or S, $R^1$ represents methyl, ethyl, n- or i-propyl, $R^2$ represents hydrogen, methyl, ethyl, methoxycarbonyl, ethoxycarbonyl, methylthio or ethylthio, $R^3$, $R^4$ independently of one another represent hydrogen, nitro, cyano, fluorine, chlorine, bromine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^5$ represents hydrogen, represents methyl, ethyl, n- or i-propyl, represents methylthio, ethylthio, n- or i-propylthio, methylsulphinyl, ethylsulphinyl, n- or i-propylsulphinyl, methylsulphonyl or ethylsulphonyl, represents in each case optionally fluorine- and/or chlorine-substituted propenyl, butenyl, propinyl or butinyl, or represents cyclopropyl, Y represents hydrogen, represents in each case optionally cyano-, fluorine-, methoxy-, ethoxy-, methoxycarbonyl- or ethoxycarbonyl-substituted methyl or ethyl, represents in each case optionally fluorine- and/or chlorine-substituted methylsulphonyl or ethylsulphonyl, represents in each case optionally cyano-, fluorine-, chlorine-, methoxy- or ethoxy-substituted acetyl, propionyl, methoxycarbonyl, ethoxycarbonyl, methylaminocarbonyl or ethylaminocarbonyl, represents dimethylaminocarbonyl, represents in each case optionally fluorine-, chlorine- or bromine-substituted propenyl, propenylcarbonyl, propinyl or propinylcarbonyl, represents in each case optionally cyano-, fluorine-, chlorine- or methyl-substituted cyclopropylcarbonyl, cyclobutylcarbonyl, cyclopentylcarbonyl, cyclohexylcarbonyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, trifluoromethyl-, methoxy-, ethoxy-, difluoromethoxy- or trifluoromethoxy-substituted phenyl, phenylsulphonyl, phenylcarbonyl, phenylmethyl, phenylmethylsulphonyl, phenylmethylcarbonyl or phenylcarbonylmethyl and Z represents amino, cyanoamino, hydrazino, represents methoxyamino, ethoxyamino, n- or i-propoxyamino, methylhydrazino, ethylhydrazino, n- or i-propylhydrazino, n-, i-, s- or t-butylhydrazino, represents N-methylmethoxyamino or dimethylhydrazino, represents in each case optionally fluorine- and/or chlorine-substituted propenyloxy, butenyloxy, propenylthio, butenylthio, propenylamino, butenylamino, propenyloxyamino, butenyloxyamino, propinyloxy, butinyloxy, propinylamino or butinylamino, represents in each case optionally cyano-, fluorine-, chlorine- or methyl-substituted cyclopropyl, cyclopentyl, cyclohexyl, cyclopropyloxy, cyclopentyloxy, cyclohexyloxy, cyclopropylamino, cyclopentylamino, cyclohexylamino, cyclohexylhydrazino, cyclopropylmethyl, cyclopentylmethyl, cyclohexylmethyl, cyclopropylmethoxy, cyclopentylmethoxy, cyclohexylmethoxy, cyclopropylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, phenylmethyl, phenylethyl, phenylmethoxy, phenylethoxy, phenylmethylthio, phenylethylthio, phenylmethylamino or phenylethylamino, or represents in each case optionally nitro-, cyano-, fluorine-, chlorine-, bromine-, methyl-, ethyl-, n- or i-propyl-, n-, i-, s- or t-butyl-, cyclopropyl-, cyclobutyl-, cyclopentyl-, cyclohexyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, heterocyclylalkyl, heterocyclylalkoxy or heterocyclylalkylamino from the group consisting of furyl, fuloxy, furylamino, furylmethyl, furylmethoxy, furylmethylamino, tetrahydrofuryl, tetrahydrofuryloxy, tetrahydrofurylamino, tetrahydrofurylmethyl, tetrahydrofurylmethoxy, tetrahydrofurylmethylamino, dioxolanyl, dioxolanylmethyl, dioxolanylmethoxy, dioxolanylmethylamino, thienyl, thienylamino, thienylmethyl, thienylmethylamino, dithiolanyl, dithiolanylmethyl, dithiolanylmethoxy, dithiolanylmethylamino, pyrrolidinyl, pyrrolidinylamino, oxo-pyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, imidazolinylmethyl, 2-oxo-1,3-diaza-cyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), thiazolyl, thiazolylmethyl, dihydrothiazolyl (thiazolinyl), tetrahydrothiazolyl (thiazolidinyl), oxothiazolidinyl, cyanoiminothiazolidinyl, oxotriazolinyl, oxotetrazolinyl, dioxanyl, dioxanylmethyl, dioxanylmethoxy, dioxanylmethylamino, dithianyl, dithianylmethyl, dithianylmethoxy, dithianylmethylamino, triazolylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, oxomorpholinyl, morpholinylamino, piperazinyl, pyridinyl, pyridinyloxy, pyridinylamino, pyridinylmethyl, pyridinylmethoxy, pyrimidinyl, pyrimidinyloxy, pyrimidinylmethyl, pyrimidinylmethoxy.

Particular emphasis is given to the compounds of the formulae (I-1) to (I-3):

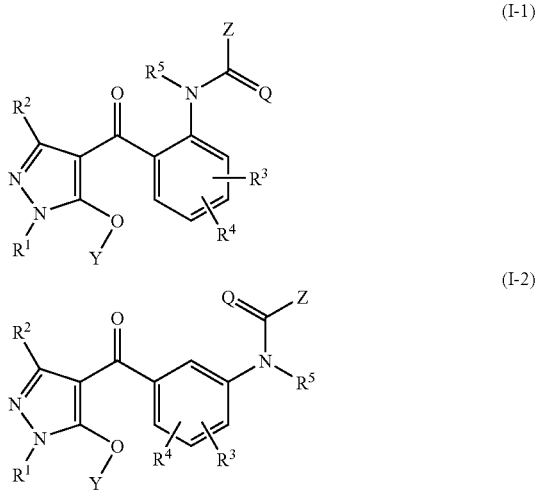

(I-1)

(I-2)

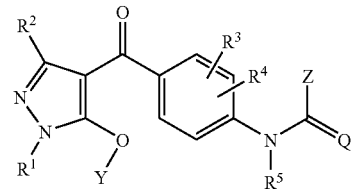

(I-3)

Here, Q, $R^1$, $R^2$, $R^3$, $R^4$, $R^5$, Y and Z in each case have the meanings given above as being preferred, particularly preferred or very particularly preferred.

Particular emphasis is also given to the compounds of the formulae (I-a), (I-b) and (I-c):

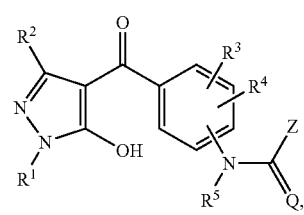

(I-a)

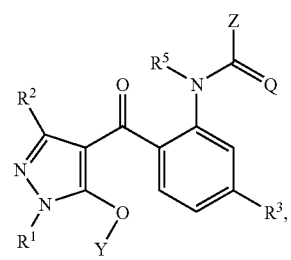

(I-b)

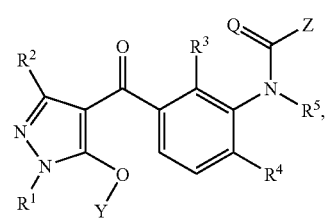

(I-c)

Here, Q, Z, $R^1$, $R^2$, $R^3$, $R^4$ and $R^5$ in each case have the meanings given above as being preferred, particularly preferred or very particularly preferred.

The general or preferred radical definitions given above apply both to the end products of the formula (I) and, correspondingly, to the starting materials or intermediates required in each case for the preparation.

The radical definitions can be combined with one another as desired, i.e. including combinations between the given preferred ranges.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Unless defined otherwise, the following definitions apply in the definitions given above and below:

Saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino. Unless indicated otherwise, preference is given to hydrocarbon chains having 1 to 6 carbon atoms.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated, unsaturated or aromatic cyclic compounds in which at least one ring atom is a heteroatom, i.e. an atom different from carbon. If the ring contains a plurality of heteroatoms, these can be identical or different. Preferred heteroatoms are oxygen, nitrogen and sulphur. If the ring contains a plurality of oxygen atoms, these are not adjacent. If appropriate, the cyclic compounds may form a polycyclic ring system together with further carbocyclic or heterocyclic fused-on or bridged rings. A polycyclic ring system can be attached via the heterocyclic ring or a fused-on carbocyclic ring. Preference is given to mono- or bicyclic ring systems, in particular to monocyclic ring systems having 5 or 6 ring members and to bicyclic ring systems having 7 to 9 ring members.

Cycloalkyl represents saturated, carbocyclic compounds which, if appropriate, form a polycyclic ring system together with further carbocyclic fused-on or bridged rings.

Unless indicated otherwise, preference is given to cyclopropyl, cyclopentyl and cyclohexyl.

The novel substituted benzoylpyrazoles of the general formula (I) have strong and selective herbicidal activity.

The novel substituted benzoylpyrazoles of the general formula (I) obtained when a) pyrazoles of the general formula (II)

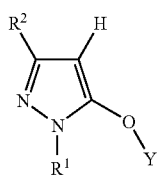

(II)

in which
R$^1$, R$^2$ and Y are as defined above
are reacted with substituted benzoic acids of the general formula (III)

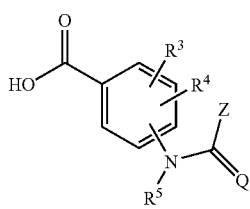

(III)

in which
Q, R$^3$, R$^4$, R$^5$ and Z are as defined above
or with reactive derivatives thereof, such as, for example, the corresponding acid halides, acid anhydrides, acid cyanides or esters,
if appropriate in the presence of a dehydrating agent, if appropriate in the presence of one or more reaction auxiliaries and if appropriate in the presence of one or more diluents, or when
(b) substituted benzoylpyrazoles of the general formula (Ia)

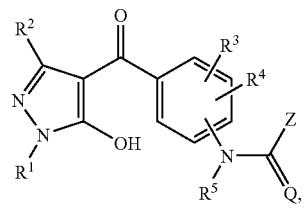

(Ia)

in which
Q, R$^1$, R$^2$, R$^3$, R$^4$, R$^5$ and Z are as defined above,
are reacted with compounds of the general formula (IV)

X—Y  (IV)

in which
Y is as defined above, except for hydrogen, and
X represents halogen,
or, if appropriate, with corresponding acid anhydrides, isocyanates or isothiocyanates
if appropriate in the presence of one or more reaction auxiliaries and if appropriate in the presence of one or more diluents,
and, if appropriate, the resulting compounds of the formula (I) are subsequently subjected, in a customary manner, to electrophilic or nucleophilic substitution reactions and/or oxidation or reduction reactions, or the compounds of the formula (I) are, in a customary manner, converted into salts.

In principle, the novel substituted benzoylpyrazoles of the general formula (I) can also be obtained as shown schematically below:

(c) by reacting aminobenzoylpyrazoles of the general formula (V) with halogeno-(thio)carbonyl compounds of the general formula (VI) or, if appropriate, with corresponding iso(thio)cyanates (here, Q, R$^1$, R$^2$, R$^3$, R$^4$, R$^5$, Y and Z are as defined above, X represents halogen):

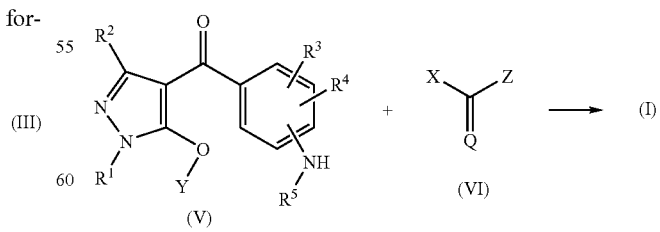

(d) by reacting iso(thio)cyanatobenzoylpyrazoles of the general formula (VII) with nucleophilic compounds of the general formula (VIII) (here, Q, R$^1$, R$^2$, R$^3$, R$^4$, Y and Z are as defined above):

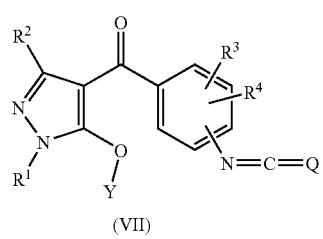

Using, for example, 3-chloro-5-hydroxy-1-methyl-pyrazol and 3-[(cyclopropylaminocarbonyl)-(methylamino)]-5-fluoro-benzoic acid as starting materials, the course of the reaction in the process (a) according to the invention can be illustrated by the formula scheme below:

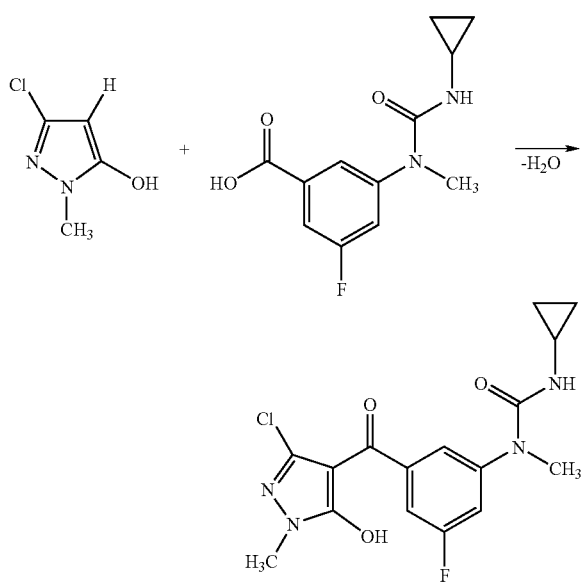

Using, for example, 2-methoxy-ethyl N-[3-chloro-4-[(1-ethyl-5-hydroxy-1H-pyrazol-4-yl)-carbonyl]-phenyl]-N-ethyl-carbamate and benzoyl chloride as starting materials, the course of the reaction in the process (b) according to the invention can be illustrated by the formula scheme below:

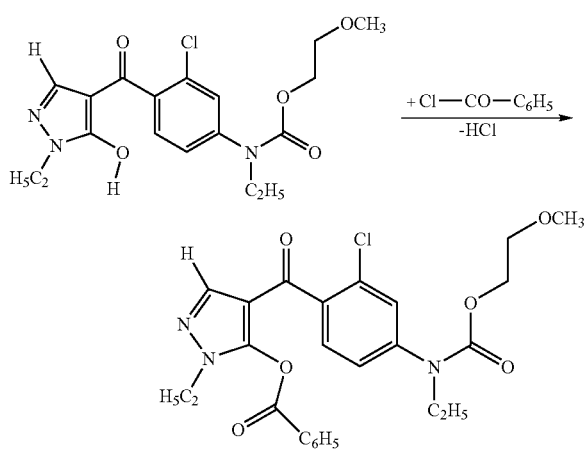

The formula (II) provides a general definition of the pyrazoles to be used as starting materials in the process (a) according to the invention for preparing compounds of the general formula (I). In the general formula (II), $R^1$, $R^2$ and Y preferably have those meanings which have already been mentioned above, in connection with the description of the compounds of the general formula (I) according to the invention, as being preferred, particularly preferred or very particularly preferred for $R^1$, $R^2$ and Y.

The starting materials of the general formula (II) are known and/or can be prepared by processes known per se (cf. EP-A-240 001).

The formula (III) provides a general definition of the substituted benzoic acids further to be used as starting materials in the process (a) according to the invention. In the formula (III) Q, $R^3$, $R^4$, $R^5$ and Z preferably have those meanings which have already been mentioned above, in connection with the description of the compounds of the formula (I) according to the invention, as being preferred, particularly preferred or very particularly preferred for Q, $R^3$, $R^4$, $R^5$ and Z.

The starting materials of the general formula (III) are known and/or can be prepared by processes per se (cf. JP-A-112 92 849 and Preparation Examples).

The substituted benzoic acids of the general formula (III) are obtained when benzoic acid esters of the general formula (IIIa)

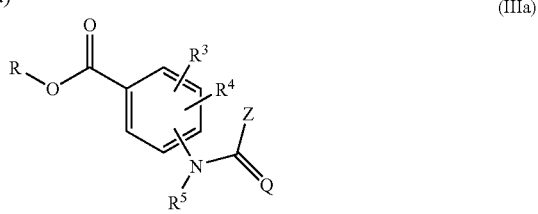

(IIIa)

in which

Q, $R^3$, $R^4$, $R^5$ and Z are as defined above and

R represents alkyl, in particular methyl or ethyl, are reacted with water, if appropriate in the presence of a hydrolysis auxiliary, such as, for example, aqueous sodium hydroxide solution, and if appropriate in the presence of a diluent, such as, for example, tetrahydrofuran, at temperatures between 0° C. and 100° C. (cf. the Preparation Examples).

The benzoic acid esters of the general formula (IIIa) required as precursors are known and/or can be prepared by processes known per se (cf. JP-A-112 92 849 and Preparation Examples).

The benzoic acid esters of the general formula (IIIa) are obtained when (α) aminobenzoic acid esters of the general formula (IX)

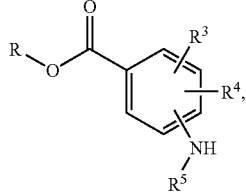

(IX)

in which

Q, $R^3$, $R^4$, $R^5$ and Z are as defined above and

R represents alkyl, in particular methyl or ethyl, are reacted with halogeno(thio)carbonyl compounds of the general formula (VI)

(VI)

in which

Q and Z are as defined above and

X represents halogen, in particular fluorine, chlorine or bromine, or, if appropriate, with the corresponding iso(thio)cyanates
if appropriate in the presence of an acid acceptor, such as, for example, potassium carbonate or triethylamine, and if appropriate in the presence of a diluent, such as, for example, methyl isobutyl ketone or acetonitrile, at temperatures between 0° C. and 100° C. (cf. the Preparation Examples), or when (β) iso(thio)cyanatobenzoic acid esters of the general formula (X)

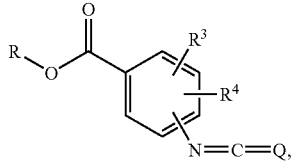

(X)

in which

Q, $R^3$ and $R^4$ are as defined above and

R represents alkyl, in particular methyl or ethyl, are reacted with nucleophilic compounds of the general formula (VIII)

(VIII)

in which

Z is as defined above, if appropriate in the presence of a reaction auxiliary, such as, for example, triethylamine, and if appropriate in the presence of a diluent, such as, for example, acetonitrile or toluene, at temperatures between 10° C. and 120° C. (cf. the Preparation Examples).

The formula (Ia) provides a general definition of the substituted benzoylpyrazoles to be used as starting materials in the process (b) according to the invention for preparing compounds of the general formula (I). In the general formula (Ia), Q, $R^1$, $R^2$, $R^3$, $R^4$, $R^5$ and Z preferably have those meanings which have already been mentioned above, in connection with the description of the compounds of the general formula (I) according to the invention, as being preferred, particularly preferred or very particularly preferred for Q, $R^1$, $R^2$, $R^3$, $R^4$, $R^5$ and Z.

The starting materials of the general formula (Ia) are novel compounds according to the invention; they can be prepared by process (a) according to the invention.

The formula (IV) provides a general definition of the compounds further to be used as starting materials in the process (b) according to the invention. In the general formula (IV), Y preferably has that meaning which has already been mentioned above, in connection with the description of the compounds of the general formula (I) according to the invention, as being preferred, particularly preferred or very particularly preferred for Y; X preferably represents fluorine, chlorine, bromine or iodine, in particular chlorine or bromine.

The starting materials of the general formula (IV) are known chemicals for synthesis.

The formulae (V) and (VI) provide general definitions of the compounds further to be used as starting materials in the process (c) according to the invention for preparing compounds of the general formula (I). In the general formulae (V) and (VI), Q, $R^1$, $R^2$, $R^3$, $R^4$, $R^5$, X and Z preferably have that meaning which has already been mentioned above, in connection with the description of the general formula (I), as being preferred, particularly preferred or very particularly preferred for Q, $R^1$, $R^2$, $R^3$, $R^4$, $R^5$, X and Z. The starting materials of the general formula (VI) are known organic compounds. The starting materials of the general formula (V) can be prepared by processes known per se.

The formulae (VII) and (VIII) provide general definitions of the compounds to be used as starting materials in the process (d) according to the invention for preparing compounds of the general formula (I). In the general formulae (VII) and (VIII), Q, $R^1$, $R^2$, $R^3$, $R^4$, $R^5$, Y and Z preferably have that meaning which has already been mentioned above, in connection with the description of the general formula (I), as being preferred, particularly preferred or very particularly preferred.

The starting materials of the general formula (VIII) are known chemicals for synthesis. The starting materials of the general formula (VII) can be prepared by processes known per se.

The formula (IX) provides a general definition of the compounds to be used as starting materials in the process (α) according to the invention for preparing compounds of the general formula (IIIa). In the general formula (IX), $R^3$, $R^4$ or $R^5$ preferably have that meaning which has already been mentioned above, in connection with the description of the general formula (I), as being preferred, particularly preferred or very particularly preferred.

The formula (X) provides a general definition of the compounds to be used as starting materials in the process (β) according to the invention for preparing compounds of the formula (IIIa). In the general formula (X), Q, $R^3$ and $R^4$ preferably have that meaning which has already been mentioned above, in connection with the description of the general formula (I), as being preferred, particularly preferred or very particularly preferred.

The starting materials of the general formula (X) can be prepared by processes know per se.

The process (a) according to the invention for preparing novel substituted benzoylpyrazoles of the general formula (I) is preferably carried out using a dehydrating agent. Suitable dehydrating agents are the customary chemicals suitable for binding water.

Examples which may be mentioned are dicyclohexylcarbodiimide, propanephosphonic anhydride and carbonyl-bis-imidazole.

Dehydrating agents which may be mentioned as being particularly suitable are dicyclohexylcarbodiimide and propanephosphonic anhydride.

The process (a) according to the invention for preparing the novel substituted benzoylpyrazoles of the general formula (I) is, if appropriate, carried out using a reaction auxiliary.

Examples of suitable reaction auxiliaries which may be mentioned are sodium cyanide, potassium cyanide, acetone cyanohydrin, 2-cyano-2-(trimethylsilyloxy)-propane and trimethylsilyl cyanide.

A reaction auxiliary which may be mentioned as being particularly suitable is trimethylsilyl cyanide.

The processes (a) and (b) according to the invention are preferably carried out using one or more reaction auxiliaries. Suitable reaction auxiliaries for the processes (a) and (b) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, N-ethylpiperidine, N-methyl-morpholine, N-ethyl-morpholine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further reaction auxiliaries suitable for the processes (a) and (b) according to the invention are phase-transfer catalysts. Examples of such catalysts which may be mentioned are:

Tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyltributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

The processes according to the invention for preparing the compounds of the general formula (I) are in each case preferably carried out using one or more diluents. Suitable diluents for carrying out the processes (a) and (b) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile propionitrile or butyronitrile; amides, such as N,N-dimethylformamide, N,N-dimethylacetamide, N-methyl-formanilide, N-methyl-pyrrolidone or hexamethyl-phosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethyelene glycol monomethyl ether, diethylene glycol monoethyl ether, mixtures thereof with water or pure water.

When carrying out the processes (a) and (b) according to the invention, the reaction temperatures can be varied within a relatively wide range. In general, the processes are carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lam ium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbaria, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal. activity and a broad active spectrum when used on the soil and on above-ground parts of plants. To a certain extent they are also suitable for the selective control of monocotyledonous and dicotyledonous weeds in monocotyledonous and di-cotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, tniks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam-formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxylmethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulphuron, anilofos, asulam, atrazine, azafenidin, azimsulphuron, beflubutarnid, benazolin (-ethyl), benfuresate, bensulphuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chl oritrofen, chlorsulphuron, chlortoluron, cinidon (-ethyl), cinmethylin, cinosulphuron, clefoxydim, clethodim, clodinafop (-propargyl), clomazone, clomeprop, clopyralid, clopyrasulphuron (-methyl), cloransulam (-methyl), cumyluron, cyanazine, cybutryne, cycloate, cyclosulphamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulphuron (-methyl), ethofumesate, ethoxyfen, ethoxysulphuron, etobenzanid, fenoxaprop (-P-ethyl), fentrazamide, flamprop (-isopropyl, -isopropyl-L, -methyl), flazasulphuron, florasulam, fluazifop (-P-butyl), fluazolate, flucarbazone (-sodium), flufenacet, flumetsulaam, flumiclorac (-pentyl), flumioxazin, flumipropyn, flumetsulam, fluometuron, fluorochloridone, fluoroglycofen (-ethyl), flupoxam, flupropacil, flurpyrsulphuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulphuron, glufosinate (-ammonium), glyphosate (-isopropylammonium), halosafen, haloxyfop (-ethoxy-ethyl, -P-methyl), hexazinone, imazamethabenz (-methyl), imazamethapyr, imazamox, imazapic, imazapyr, imazaquin, imazethapyr, imazosulphuron, iodosulphuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulphuron, mesotrione, metamitron, metazachlor, methabenzthiazuron, metobenzuron, metobromuron, (alpha-) metolachlor, metosulam, metoxuron, metribuzin, metsulphuron (-methyl), molinate, monolinuron, naproanilide, napropamide, neburon, nicosulphuron, norflurazon, orbencarb, oryzalin, oxadiargyl, oxadiazon, oxasulphuron, oxaziclomefone, oxyfluorfen, paraquat, pelargon acid, pendimetha in, pendralin, pentoxazone, phenmedipham, picolinafen, piperophos, pretilachlor, primisulphuron (-methyl), profluazol, prometryn, propachlor, propanil, propaquizofop, propisochlor, procarbazone (-sodium), propyzamide, prosulphocarb, prosulphuron, pyraflufen (-ethyl), pyrazogyl, pyrazolate, pyrazosulphuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulphuron, sethoxydim, simazine, simetryn, sulcotrione, sulphentrazone, sulphometuron (-methyl), sulphosate, sulphosulphuron, tebutam, tebuthiuron, tepraloxydim, terbuthylazine, terbutryn, thenylchlor, thiafluamide, thiazopyr, thidiazimin, thifensulphuron (-methyl), thiobencarb, tiocarbazil, tralkoxydim, triallate, triasulphuron, tribenuron (-methyl), triclopyr, tridiphane, trifluralin, trifloxysulphuron, triflusulphuron (-methyl), tritosulphuron.

Furthermore suitable for the mixtures are known softeners, for example

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agro-chemical active compounds—, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or process-ability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention, where in addition to the good control of weed plants, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The following examples show the preparation and use of the active compounds according to the invention:

PREPARATION EXAMPLES

Example 1

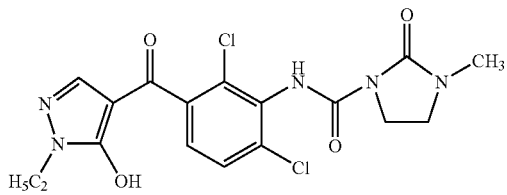

(Process (a))

A mixture of 2.80 g (8.43 mMol) of 2,4-dichloro-3-[[(3-methyl-2-oxo-1-imidazolidinyl)-carbonyl]-amino]-benzoic acid, 0.945 g (8.43 mMol) of 1-ethyl-5-hydroxy-pyrazole, 2.10 g (10.1 mmol) of dicyclohexylcarbodiimide and 30 ml of acetonitrile is stirred at room temperature (about 20° C.) for 18 hours and then filtered. 0.335 g (3.37 mMol) of trimethylsilyl cyanide and 1.70 g (16.9 mMol) of triethylamine are added to the filtrate and the mixture is stirred at room temperature for 18 hours and then concentrated under reduced pressure. The residue is stirred with 10% strength aqueous sodium carbonate solution and then shaken with diethyl ether. The organic phase is separated off (and discarded) and the aqueous solution is then acidified with conc. hydrochloric acid, and the resulting crystalline product is isolated by filtration with suction.

This gives 1.60 g (32.5% of theory) of N-[2,6-dichloro-3-[(1-ethyl-5-hydroxy-1H-pyrazol-4-yl)-carbonyl]-phenyl]-3-methyl-2-oxo-1-imidazolidinecarboxamide.

logP (pH=2.3): 1.58.

Analogously to Example 1, and in accordance with the general description of the preparation process according to the invention, it is also possible to prepare, for example, the compounds of the general formula (I)—or of the formulae (I-1), (I-2) or (I-3)—listed in Table I below.

TABLE 1

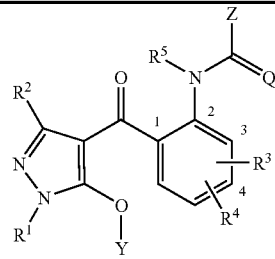
(I-1)

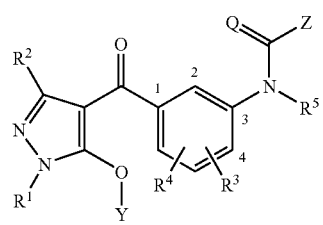
(I-2)

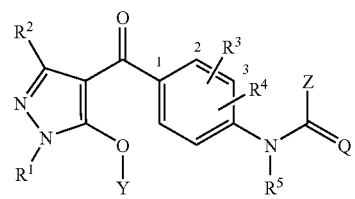
(I-3)

Examples of the compounds of the formulae (I), (I-1), (I-2), (I-3)
Here, Y in each case represents hydrogen

| Ex.-No. | Q | $R^1$ | $R^2$ | (position) $R^3$ | (position) $R^4$ | $R^5$ | Z | Formula Physical Data |
|---|---|---|---|---|---|---|---|---|
| 2 | O | $C_2H_5$ | H | (2) Cl | (4) Cl | H | OCH$_3$, N, CH$_3$ | (I-2) logP = 1,39[a] |
| 3 | O | $CH_3$ | H | (2) Cl | (4) Cl | H | OCH$_3$, N, CH$_3$ | (I-2) logP = 1.13[a] |

TABLE 1-continued
| | | | | | | | | |
|---|---|---|---|---|---|---|---|---|
| 4 | O | CH₃ | H | (2) Cl | (4) Cl | H | 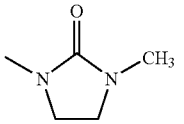 | (I-2) logP = 1.32[a] |
| 5 | O | C₂H₅ | H | (2) Cl | (4) Cl | H | 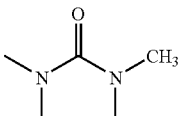 | (I-2) logP = 1.83[a] |
| 6 | O | C₂H₅ | H | (2) Cl | (4) Cl | H | 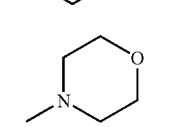 | (I-2) logP = 1.13[a] |
| 7 | O | C₂H₅ | H | (4) CF₃ | — | H | 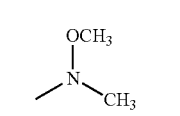 | (I-1) logP = 2.93[a] |
| 8 | O | CH₃ | H | (4) CF₃ | — | H | 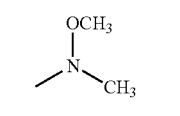 | (I-1) logP = 2.50[a] |
| 9 | O | CH₃ | H | (2) Cl | (4) Cl | H | 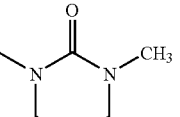 | (I-2) logP = 1.55[a] |
| 10 | O | CH₃ | H | (2) Cl | (4) Cl | H | 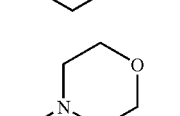 | (I-2) logP = 0.82[a] |
| 11 | O | C₂H₅ | H | (4) CF₃ | — | H | 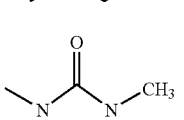 | (I-1) logP = 2.42[a] |
| 12 | O | CH₃ | H | (2) Cl | (4) Cl | H | 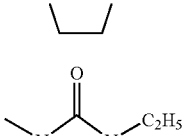 | (I-2) logP = 1.63[a] |
| 13 | O | C₂H₅ | H | (2) Cl | (4) Cl | H | 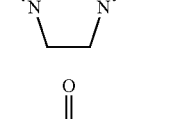 | (I-2) logP = 1.86[a] |
| 14 | O | C₂H₅ | H | (2) Cl | (4) Cl | H | 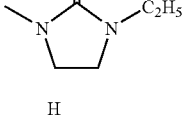 | (I-2) logP = 1.25[a] |
| 15 | O | CH₃ | H | (2) Cl | (4) Cl | H | 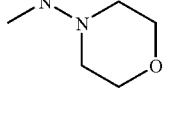 | (I-2) logP = 1.03[a] |

TABLE 1-continued

| 16 | O | CH₃ | H | (2) Cl | (4) Cl | H | ![structure: N-methyl-N-pyrrolidin-1-yl-amine] | (I-2) logP = 1.17[a] |
| 17 | O | CH₃ | H | (4) CF₃ | — | H | ![structure: 1,3-dimethylimidazolidin-2-one] | (I-1) logP = 2.12[a] |
| 18 | O | C₂H₅ | H | (2) Cl | (4) Cl | H | ![structure: 1-methyl-3-ethyl-tetrahydropyrimidin-2-one] | (I-2) logP = 2.11[a] |
| 19 | O | CH₃ | H | (2) Cl | (4) Cl | H | ![structure: 1-methyl-3-ethyl-tetrahydropyrimidin-2-one] | (I-2) logP = 1.83[a] |
| 20 | O | CH₃ | H | (2) Cl | (4) Cl | H | ![structure: 1,4-dimethylpiperazine] | (I-2) |
| 21 | O | CH₃ | H | (2) Cl | (4) Cl | H | ![structure: N-methyl-cyclopropylamine] | (I-2) logP = 0.99[a] |
| 22 | O | CH₃ | H | (2) Cl | (4) Cl | H | ![structure: N-methyl-cyclopentylamine] | (I-2) |
| 23 | O | CH₃ | H | (2) Cl | (4) Cl | H | ![structure: N-methyl-cyclohexylamine] | (I-2) |
| 24 | O | CH₃ | H | (2) Cl | (4) Cl | H | ![structure: 1-methyl-pyrrolidine] | (I-2) logP = 1.18[a] |
| 25 | O | CH₃ | H | (2) Cl | (4) Cl | H | ![structure: 1-methyl-3-n-propylimidazolidin-2-one] | (I-2) |
| 26 | O | CH₃ | H | (2) Cl | (4) Cl | H | ![structure: 1-methyl-3-isopropylimidazolidin-2-one] | (I-2) |

TABLE 1-continued
| 27 | O | CH₃ | H | (2) Cl | (4) Cl | H | 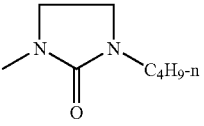 | (I-2) |
| 28 | O | CH₃ | H | (2) Cl | (4) Cl | H | 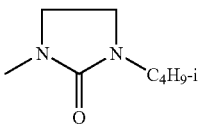 | (I-2) |
| 29 | O | CH₃ | H | (2) Cl | (4) Cl | H | 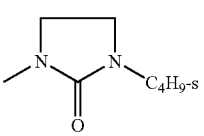 | (I-2) |
| 30 | O | CH₃ | H | (2) Cl | (4) Cl | H | 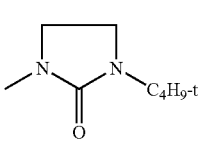 | (I-2) |
| 31 | O | CH₃ | H | (2) Cl | (4) Cl | H | 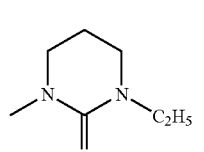 | (I-2) |
| 32 | O | CH₃ | H | (2) Cl | (4) Cl | H | 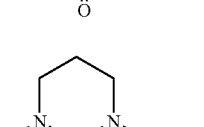 | (I-2) |
| 33 | O | CH₃ | H | (2) Cl | (4) Cl | H | 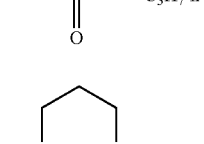 | (I-2) logP = 2.11[a] |
| 34 | O | CH₃ | H | (2) Cl | (4) Cl | H | 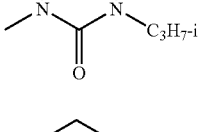 | (I-2) |
| 35 | O | CH₃ | H | (2) Cl | (4) Cl | H | 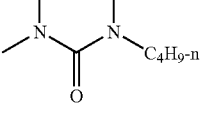 | (I-2) |
| 36 | O | CH₃ | H | (2) Cl | (4) Cl | H | 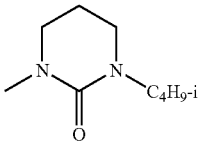 | (I-2) |

TABLE 1-continued
| 37 | O | CH$_3$ | H | (2) Cl | (4) Cl | H | 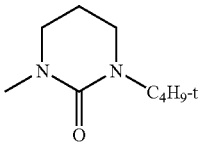 | (I-2) |
| 38 | O | CH$_3$ | H | (2) Cl | (4) Cl | H | 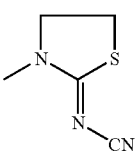 | (I-2) |
| 39 | O | CH$_3$ | H | (2) Cl | (4) Cl | H | 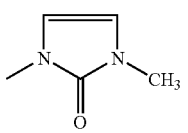 | (I-2) |
| 40 | O | CH$_3$ | H | (2) Cl | (4) Cl | H | 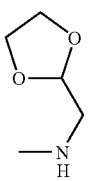 | (I-2) |
| 41 | O | CH$_3$ | H | (2) Cl | (4) Cl | H | 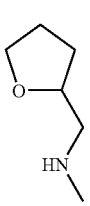 | (I-2) logP = 1.10$^{a)}$ |
| 42 | O | CH$_3$ | H | (2) Cl | (4) Cl | H | 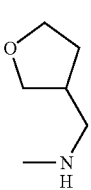 | (I-2) |
| 43 | O | CH$_3$ | H | (2) Cl | (4) Cl | H | 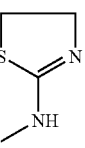 | (I-2) |
| 44 | O | CH$_3$ | H | (2) Cl | (4) Cl | H | 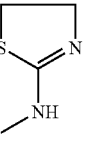 | (I-2) |
| 45 | O | CH$_3$ | H | (2) Cl | (4) Cl | H | 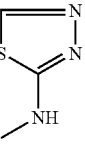 | (I-2) |

TABLE 1-continued

| 46 | O | CH₃ | H | (2) Cl | (4) Cl | H | H₃C-[1,3,4-thiadiazole]-NH-CH₃ | (I-2) |
| 47 | O | CH₃ | H | (2) Cl | (4) Cl | H | F₃C-[1,3,4-thiadiazole]-NH-CH₃ | (I-2) logP = 1.99ᵃ⁾ |
| 48 | O | CH₃ | H | (2) Cl | (4) Cl | H | [1,3,4-oxadiazole]-NH-CH₃ | (I-2) |
| 49 | O | CH₃ | H | (2) Cl | (4) Cl | H | [isoxazole]-NH-CH₃ | (I-2) |
| 50 | O | CH₃ | H | (2) Cl | (4) SO₂CH₃ | H | 1,3-dimethylimidazolidin-2-one | (I-2) |
| 51 | O | CH₃ | H | (2) Cl | (4) SO₂CH₃ | H | 1-methyl-3-ethyl-tetrahydropyrimidin-2-one | (I-2) |
| 52 | O | CH₃ | H | (2) Cl | (4) SO₂CH₃ | H | 1,4-dimethylpiperazine | (I-2) |
| 53 | O | CH₃ | H | (2) Cl | (4) SO₂CH₃ | H | cyclopropyl-NH-CH₃ | (I-2) |
| 54 | O | CH₃ | H | (2) Cl | (4) SO₂CH₃ | H | cyclopentyl-NH-CH₃ | (I-2) |
| 55 | O | CH₃ | H | (2) Cl | (4) SO₂CH₃ | H | cyclohexyl-NH-CH₃ | (I-2) |

TABLE 1-continued

| | | | | | | | | |
|---|---|---|---|---|---|---|---|---|
| 56 | O | CH$_3$ | H | (2) Cl | (4) SO$_2$CH$_3$ | H | N-methylpyrrolidinyl | (I-2) |
| 57 | O | CH$_3$ | H | (2) Cl | (4) SO$_2$CH$_3$ | H | 1-methyl-3-(n-C$_3$H$_7$)-imidazolidin-2-one | (I-2) |
| 58 | O | CH$_3$ | H | (2) Cl | (4) SO$_2$CH$_3$ | H | 1-methyl-3-(i-C$_3$H$_7$)-imidazolidin-2-one | (I-2) |
| 59 | O | CH$_3$ | H | (2) Cl | (4) SO$_2$CH$_3$ | H | 1-methyl-3-(n-C$_4$H$_9$)-imidazolidin-2-one | (I-2) |
| 60 | O | CH$_3$ | H | (2) Cl | (4) SO$_2$CH$_3$ | H | 1-methyl-3-(i-C$_4$H$_9$)-imidazolidin-2-one | (I-2) |
| 61 | O | CH$_3$ | H | (2) Cl | (4) SO$_2$CH$_3$ | H | 1-methyl-3-(s-C$_4$H$_9$)-imidazolidin-2-one | (I-2) |
| 62 | O | CH$_3$ | H | (2) Cl | (4) SO$_2$CH$_3$ | H | 1-methyl-3-(t-C$_4$H$_9$)-imidazolidin-2-one | (I-2) |
| 63 | O | CH$_3$ | H | (2) Cl | (4) SO$_2$CH$_3$ | H | 1-methyl-3-ethyl-tetrahydropyrimidin-2-one | (I-2) |
| 64 | O | CH$_3$ | H | (2) Cl | (4) SO$_2$CH$_3$ | H | 1-methyl-3-(n-C$_3$H$_7$)-tetrahydropyrimidin-2-one | (I-2) |
| 65 | O | CH$_3$ | H | (2) Cl | (4) SO$_2$CH$_3$ | H | 1-methyl-3-(i-C$_3$H$_7$)-tetrahydropyrimidin-2-one | (I-2) |
| 66 | O | CH$_3$ | H | (2) Cl | (4) SO$_2$CH$_3$ | H | 1-methyl-3-(n-C$_4$H$_9$)-tetrahydropyrimidin-2-one | (I-2) |

TABLE 1-continued

| No. | | | | | | | Structure | |
|---|---|---|---|---|---|---|---|---|
| 67 | O | CH₃ | H | (2) Cl | (4) SO₂CH₃ | H | N-methyl, N-iC₄H₉ tetrahydropyrimidin-2-one | (I-2) |
| 68 | O | CH₃ | H | (2) Cl | (4) SO₂CH₃ | H | N-methyl, N-sC₄H₉ tetrahydropyrimidin-2-one | (I-2) |
| 69 | O | CH₃ | H | (2) Cl | (4) SO₂CH₃ | H | N-methyl, N-tC₄H₉ tetrahydropyrimidin-2-one | (I-2) |
| 70 | O | CH₃ | H | (2) Cl | (4) SO₂CH₃ | H | N-methyl-2-(cyanoimino)thiazolidine | (I-2) |
| 71 | O | CH₃ | H | (2) Cl | (4) SO₂CH₃ | H | 1,3-dimethyl-2,3-dihydro-1H-imidazol-2-one | (I-2) |
| 72 | O | CH₃ | H | (2) Cl | (4) SO₂CH₃ | H | (1,3-dioxolan-2-yl)methyl-NH- | (I-2) |
| 73 | O | CH₃ | H | (2) Cl | (4) SO₂CH₃ | H | (tetrahydrofuran-2-yl)methyl-NH- | (I-2) |
| 74 | O | CH₃ | H | (2) Cl | (4) SO₂CH₃ | H | (tetrahydrofuran-3-yl)methyl-NH- | (I-2) |
| 75 | O | CH₃ | H | (2) Cl | (4) SO₂CH₃ | H | 2-(methylamino)-4,5-dihydrothiazole | (I-2) |

TABLE 1-continued
| 76 | O | CH₃ | H | (2) Cl | (4) SO₂CH₃ | H | 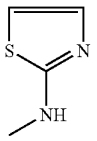 | (I-2) |
| 77 | O | CH₃ | H | (2) Cl | (4) SO₂CH₃ | H | 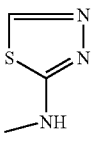 | (I-2) |
| 78 | O | CH₃ | H | (2) Cl | (4) SO₂CH₃ | H | 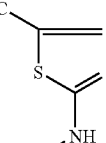 | (I-2) |
| 79 | O | CH₃ | H | (2) Cl | (4) SO₂CH₃ | H | 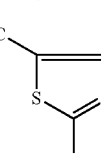 | (I-2) |
| 80 | O | CH₃ | H | (2) Cl | (4) SO₂CH₃ | H | 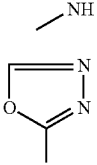 | (I-2) |
| 81 | O | CH₃ | H | (2) Cl | (4) SO₂CH₃ | H | 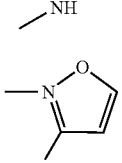 | (I-2) |
| 82 | O | CH₃ | H | (2) Cl | (4) SO₂CH₃ | H | 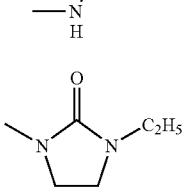 | (I-2) |
| 83 | O | CH₃ | H | (2) Cl | (4) SO₂CH₃ | H | 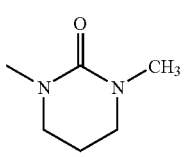 | (I-2) |
| 84 | O | CH₃ | H | (2) Cl | (4) SO₂CH₃ | H | 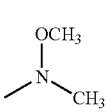 | (I-2) |
| 85 | O | CH₃ | H | (2) Cl | (4) SO₂CH₃ | H |  | (I-2) |
| 86 | O | CH₃ | H | (2) Cl | (4) SO₂CH₃ | H | 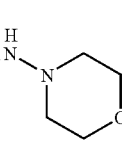 | (I-2) |

TABLE 1-continued
| 87 | O | CH₃ | H | (2) Cl | (4) SO₂CH₃ | H | 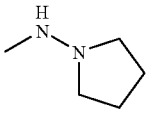 | (I-2) |
| 88 | O | CH₃ | H | (4) CF₃ | — | H | 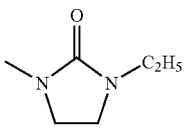 | (I-1) |
| 89 | O | CH₃ | H | (4) CF₃ | — | H | 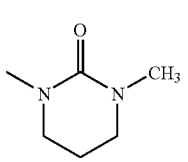 | (I-1) |
| 90 | O | C₂H₅ | H | (4) CF₃ | — | H | 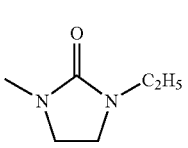 | (I-1) |
| 91 | O | CH₃ | H | (4) CF₃ | — | H | 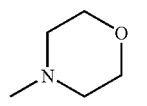 | (I-1) |
| 92 | O | CH₃ | H | (4) CF₃ | — | H | 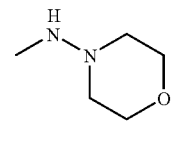 | (I-1) |
| 93 | O | CH₃ | H | (4) CF₃ | — | H | 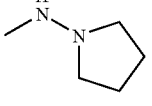 | (I-1) |
| 94 | O | CH₃ | H | (4) CF₃ | — | H | 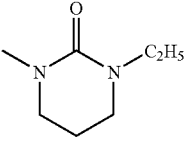 | (I-1) |
| 95 | O | C₂H₅ | H | (4) CF₃ | — | H | 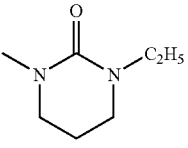 | (I-1) |
| 96 | O | C₂H₅ | H | (4) CF₃ | — | H | 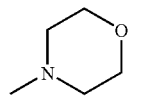 | (I-1) |
| 97 | O | CH₃ | H | (4) CF₃ | — | H | 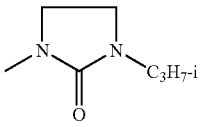 | (I-1) |

TABLE 1-continued

| | | | | | | | | |
|---|---|---|---|---|---|---|---|---|
| 98 | O | C$_2$H$_5$ | H | (4) CF$_3$ | — | H | N-methyl-N'-isopropyl imidazolidinone | (I-1) |
| 99 | O | C$_2$H$_5$ | H | (2) Cl | (4) Cl | CH$_3$ | 1,3-dimethyl imidazolidinone | (I-2) logP = 1.40$^{a)}$ |
| 100 | O | C$_2$H$_5$ | H | (2) Cl | (4) Cl | H | N-methyl-pyrrolidinylamine | (I-2) logP = 1.42$^{a)}$ |
| 101 | O | C$_2$H$_5$ | H | (2) Cl | (4) Cl | H | N-methyl-N'-isopropyl tetrahydropyrimidinone | (I-2) logP = 2.42$^{a)}$ |
| 102 | O | C$_2$H$_5$ | H | (2) Cl | (4) Cl | H | N-methyl-N'-cyclohexyl tetrahydropyrimidinone | (I-2) logP = 3.30$^{a)}$ |
| 103 | O | C$_2$H$_5$ | H | (4) CF$_3$ | — | CH$_3$ | 1,3-dimethyl imidazolidinone | (I-1) logP = 1.78$^{a)}$ |
| 104 | O | C$_2$H$_5$ | H | (2) Cl | (4) Cl | H | N-cyclopropyl-methylamine | (I-2) logP = 1.25$^{a)}$ |
| 105 | O | C$_2$H$_5$ | H | (2) Cl | (4) Cl | H | N-methyl-(tetrahydrofuran-2-yl)methylamine | (I-2) logP = 1.33$^{a)}$ |
| 106 | O | C$_2$H$_5$ | H | (2) Cl | (4) Cl | H | N-methylpiperidine | (I-2) logP = 1.75$^{a)}$ |
| 107 | O | CH$_3$ | H | (2) Cl | (4) Cl | H | N-methylpiperidine | (I-2) logP = 1.50$^{a)}$ |
| 108 | O | C$_2$H$_5$ | H | (2) Cl | (4) Cl | H | N-methyl-O-methylhydroxylamine | (I-2) logP = 1.06$^{a)}$ |
| 109 | O | CH$_3$ | H | (2) Cl | (4) Cl | H | N-methyl-O-methylhydroxylamine | (I-2) logP = 0.72$^{a)}$ |

TABLE 1-continued
| 110 | O | C₂H₅ | H | (2) Cl | (4) Cl | H | 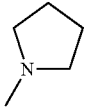 | (I-2) logP = 1.52[a] |
| --- | --- | --- | --- | --- | --- | --- | --- | --- |
| 111 | O | C₂H₅ | H | (2) OCH₃ | — | H | 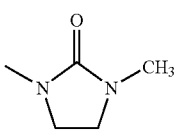 | (I-3) logP = 1.74[a] |
| 112 | O | C₂H₅ | H | (2) Cl | (4) Cl | H | 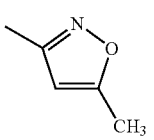 | (I-2) logP = 1.82[a] |
| 113 | O | CH₃ | H | (2) Cl | (4) Cl | H |  | (I-2) |
| 114 | O | C₂H₅ | H | (2) Cl | (4) Cl | H |  | (I-2) |
| 115 | O | CH₃ | CH₃ | (2) Cl | (4) Cl | H |  | (I-2) |
| 116 | O | CH₃ | 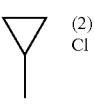 | (2) Cl | (4) Cl | H |  | (I-2) |
| 117 | O | C₃H₇-i | H | (2) Cl | (4) Cl | H |  | (I-2) |
| 118 | O | 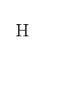 | H | (2) Cl | (4) Cl | H |  | (I-2) |
| 119 | O | CH₃ | CH₃ | (2) Cl | (4) Cl | H |  | (I-2) |
| 120 | O | CH₃ |  | (2) Cl | (4) Cl | H |  | (I-2) |
| 121 | O | C₃H₇-i | H | (2) Cl | (4) Cl | H |  | (I-2) |
| 122 | O |  | H | (2) Cl | (4) Cl | H |  | (I-2) |
| 123 | O | CH₃ | CH₃ | (2) Cl | (4) Cl | H | 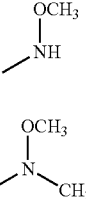 | (I-2) |

TABLE 1-continued
| | | | | | | | |
|---|---|---|---|---|---|---|---|
| 124 | O | CH₃ |  | (2) Cl | (4) Cl | H | 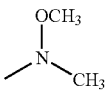 (I-4) |
| 125 | O | C₃H₇-i | H | (2) Cl | (4) Cl | H | 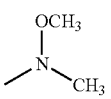 (I-2) |
| 126 | O |  | H | (2) Cl | (4) Cl | H | 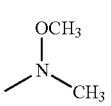 (I-2) |
| 127 | O | CH₃ | H | (2) Cl | (4) Cl | H | 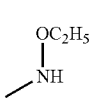 (I-2) logP = 1.07[a] |
| 128 | O | C₂H₅ | H | (2) Cl | (4) Cl | H | 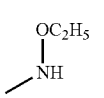 (I-2) logP = 1.33[a] |
| 129 | O | CH₃ | H | (2) Cl | (4) Cl | H | 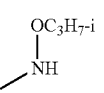 (I-2) |
| 130 | O | C₂H₅ | H | (2) Cl | (4) Cl | H | 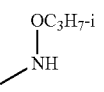 (I-2) |
| 131 | O | CH₃ | H | (2) Cl | (4) Cl | H | 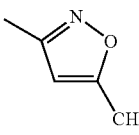 (I-2) |
| 132 | O | C₂H₅ | H | (2) Cl | (4) Cl | H | 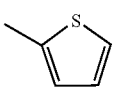 (I-2) |
| 133 | O | CH₃ | H | (2) Cl | (4) Cl | H | 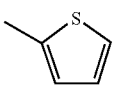 (I-2) |
| 134 | O | CH₃ | CH₃ | (2) Cl | (4) Cl | H | 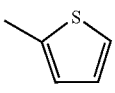 (I-2) |
| 135 | O | CH₃ |  | (2) Cl | (4) Cl | H | 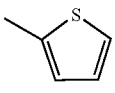 (I-2) |
| 136 | O | C₃H₇-i | H | (2) Cl | (4) Cl | H | 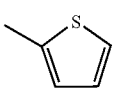 (I-2) |
| 137 | O |  | H | (2) Cl | (4) Cl | H | 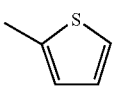 (I-2) |
| 138 | O | CH₃ | CH₃ | (2) Cl | (4) Cl | H | 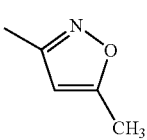 (I-2) |

TABLE 1-continued
| | | | | | | | |
|---|---|---|---|---|---|---|---|
| 139 | O | CH₃ |  | (2) Cl | (4) Cl | H | 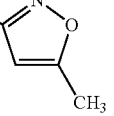 (I-2) |
| 140 | O | C₃H₇-i | H | (2) Cl | (4) Cl | H | 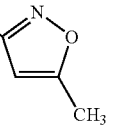 (I-2) |
| 141 | O |  | H | (2) Cl | (4) Cl | H | 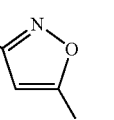 (I-2) |
| 142 | O | C₂H₅ | H | (2) Cl | (4) Cl | H | 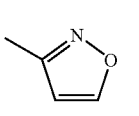 (I-2) |
| 143 | O | CH₃ | H | (2) Cl | (4) Cl | H | 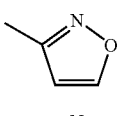 (I-2) |
| 144 | O | CH₃ | CH₃ | (2) Cl | (4) Cl | H | 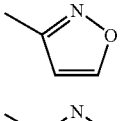 (I-2) |
| 145 | O | CH₃ |  | (2) Cl | (4) Cl | H | 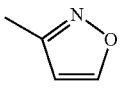 (I-2) |
| 146 | O | C₃H₇-i | H | (2) Cl | (4) Cl | H | 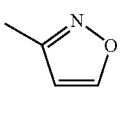 (I-2) |
| 147 | O |  | H | (2) Cl | (4) Cl | H | 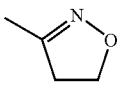 (I-2) |
| 148 | O | C₂H₅ | H | (2) Cl | (4) Cl | H | 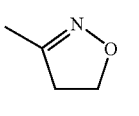 (I-2) logP = 1.45[a] |
| 149 | O | CH₃ | H | (2) Cl | (4) Cl | H | 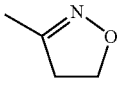 (I-2) logP = 1.18[a] |
| 150 | O | CH₃ | CH₃ | (2) Cl | (4) Cl | H | 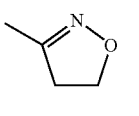 (I-2) |
| 151 | O | CH₃ |  | (2) Cl | (4) Cl | H | 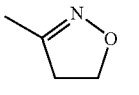 (I-2) |
| 152 | O | C₃H₇-i | H | (2) Cl | (4) Cl | H | 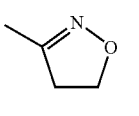 (I-2) |
| 153 | O |  | H | (2) Cl | (4) Cl | H |  (I-2) |

TABLE 1-continued

| | | | | | | | | |
|---|---|---|---|---|---|---|---|---|
| 154 | O | C$_2$H$_5$ | H | (2) Cl | (4) Cl | H | phenyl | (I-2) |
| 155 | O | C$_2$H$_5$ | H | (2) Cl | (4) Cl | H | pyridin-3-yl | (I-2) |
| 156 | O | C$_2$H$_5$ | H | (2) Cl | (4) Cl | H | furan-2-yl | (I-2) logP = 1.54[a] |
| 157 | O | C$_2$H$_5$ | H | (2) Cl | (4) Cl | H | 2-chlorophenyl | (I-2) |
| 158 | O | C$_2$H$_5$ | H | (2) Cl | (4) Cl | H | 3-chlorophenyl | (I-2) |
| 159 | O | C$_2$H$_5$ | H | (2) Cl | (4) Cl | H | 4-chlorophenyl | (I-2) logP = 2.37[a] |
| 160 | O | C$_2$H$_5$ | H | (2) Cl | (4) Cl | H | 3-(trifluoromethyl)phenyl | (I-2) |
| 161 | O | CH$_3$ | H | (2) Cl | (4) Cl | H | isoxazolidin-2-yl | (I-2) logP = 1.11[a] |
| 162 | O | C$_2$H$_5$ | H | (2) Cl | (4) Cl | H | isoxazolidin-2-yl | (I-2) logP = 1.38[a] |
| 163 | S | CH$_3$ | H | (2) Cl | (4) Cl | H | isoxazolidin-2-yl | (I-2) |
| 164 | S | C$_2$H$_5$ | H | (2) Cl | (4) Cl | H | isoxazolin-2-yl | (I-2) |
| 165 | O | C$_2$H$_5$ | H | (4) CF$_3$ | — | H | isoxazolidin-2-yl | (I-1) |
| 166 | O | CH$_3$ | H | (2) NO$_2$ | — | H | isoxazolidin-2-yl | (I-3) |
| 167 | O | CH$_3$ | H | (4) CF$_3$ | — | H | isoxazolidin-2-yl | (I-1) |

TABLE 1-continued
| | | | | | | | | |
|---|---|---|---|---|---|---|---|---|
| 168 | O | C₂H₅ | H | (2) NO₂ | — | H |  | (I-3) |
| 169 | O | CH₃ | H | (2) OCH₃ | — | H |  | (I-1) |
| 170 | O | C₂H₅ | H | (2) OCH₃ | — | H |  | (I-1) |
| 171 | O | C₂H₅ | H | (2) Cl | (4) Cl | CH₃ | 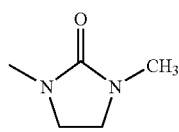 | (I-2) logP = 2.88$^{a)}$ |
| 172 | O | C₂H₅ | H | (2) Cl | (4) Cl | H | 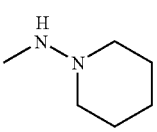 | (I-2) logP = 1.96$^{a)}$ |
| 173 | O | CH₃ | H | (2) Cl | (4) Cl | H | 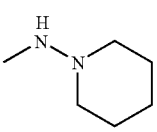 | (I-2) logP = 1.70$^{a)}$ |
| 174 | O | C₂H₅ | H | (2) Cl | (4) Cl | H | 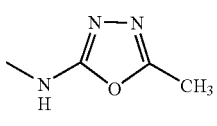 | (I-2) logP = 1.20$^{a)}$ |
| 175 | O | C₂H₅ | H | (2) Cl | (4) Cl | H | 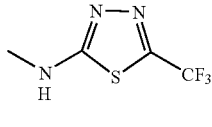 | (I-2) logP = 2.24$^{a)}$ |
| 176 | O | C₂H₅ | H | (2) Cl | (4) Cl | H | 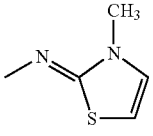 | (I-2) logP = 1.39$^{a)}$ |
| 177 | O | CH₃ | H | (2) Cl | (4) Cl | H | 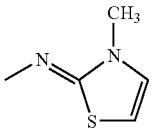 | (I-2) logP = 1.13$^{a)}$ |
| 178 | O | CH₃ | H | (2) Cl | (4) Cl | H | 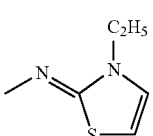 | (I-2) logP = 1.43$^{a)}$ |
| 179 | O | C₂H₅ | H | (2) Cl | (4) Cl | H | 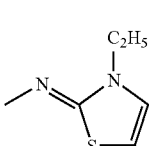 | (I-2) logP = 1.72$^{a)}$ |

TABLE 1-continued
| | | | | | | | | |
|---|---|---|---|---|---|---|---|---|
| 180 | O | C₂H₅ | H | (2) Cl | (4) Cl | H | 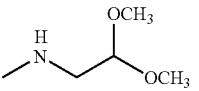 | (I-2) logP = 1.13[a] |
| 181 | O | C₂H₅ | H | (2) Cl | (4) Cl | H | 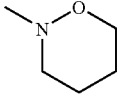 | (I-2) logP = 1.63[a] |
| 182 | O | CH₃ | H | (2) Cl | (4) Cl | H | 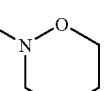 | (I-2) logP = 1.36[a] |
| 183 | O | C₂H₅ | CH₃ | (2) Cl | (4) Cl | H | 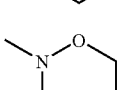 | (I-2) logP = 1.53[a] |
| 184 | O | CH₃ | CH₃ | (2) Cl | (4) Cl | H | 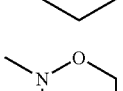 | (I-2) logP = 1.34[a] |
| 185 | O | CH₃ | CH₃ | (2) Cl | (4) Cl | H | 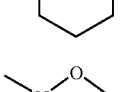 | (I-2) logP = 1.10[a] |
| 186 | O | C₂H₅ | CH₃ | (2) Cl | (4) Cl | H | 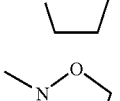 | (I-2) logP = 1.31[a] |
| 187 | O | CH₃ | H | (2) Cl | (4) Cl | H | 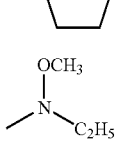 | (I-2) |
| 188 | O | C₂H₅ | H | (2) Cl | (4) Cl | H | 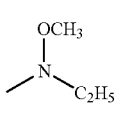 | (I-2) |
| 189 | O | CH₃ | CH₃ | (2) Cl | (4) Cl | H | 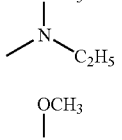 | (I-2) |
| 190 | O | C₂H₅ | CH₃ | (2) Cl | (4) Cl | H | 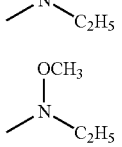 | (I-2) |
| 191 | O | CH₃ | H | (2) Cl | (4) SO₂CH₃ | H |  | (I-2) |
| 192 | O | C₂H₅ | H | (2) Cl | (4) SO₂CH₃ | H | 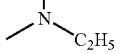 | (I-2) |
| 193 | O | CH₃ | CH₃ | (2) Cl | (4) SO₂CH₃ | H |  | (I-2) |
| 194 | O | C₂H₅ | CH₃ | (2) Cl | (4) SO₂CH₃ | H | 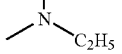 | (I-2) |

TABLE 1-continued

| 195 | O | CH₃ | H | (2) Cl | (4) Cl | H | OC₂H₅, N(CH₃)(CH₃) | (I-2) |
| 196 | O | C₂H₅ | H | (2) Cl | (4) Cl | H | OC₂H₅, N(CH₃)(CH₃) | (I-2) |
| 197 | O | CH₃ | CH₃ | (2) Cl | (4) Cl | H | OC₂H₅, N(CH₃)(CH₃) | (I-2) |
| 198 | O | C₂H₅ | CH₃ | (2) Cl | (4) Cl | H | OC₂H₅, N(CH₃)(CH₃) | (I-2) |
| 199 | O | CH₃ | H | (2) Cl | (4) SO₂CH₃ | H | OC₂H₅, N(CH₃)(CH₃) | (I-2) |
| 200 | O | C₂H₅ | H | (2) Cl | (4) SO₂CH₃ | H | OC₂H₅, N(CH₃)(CH₃) | (I-2) |
| 201 | O | CH₃ | CH₃ | (2) Cl | (4) SO₂CH₃ | H | OC₂H₅, N(CH₃)(CH₃) | (I-2) |
| 202 | O | C₂H₅ | CH₃ | (2) Cl | (4) SO₂CH₃ | H | OC₂H₅, N(CH₃)(CH₃) | (I-2) |
| 203 | O | CH₃ | H | (2) Cl | (4) Cl | H | OC₂H₅, N(CH₃)(C₂H₅) | (I-2) |
| 204 | O | C₂H₅ | H | (2) Cl | (4) Cl | H | OC₂H₅, N(CH₃)(C₂H₅) | (I-2) |
| 205 | O | CH₃ | CH₃ | (2) Cl | (4) Cl | H | OC₂H₅, N(CH₃)(C₂H₅) | (I-2) |
| 206 | O | C₂H₅ | CH₃ | (2) Cl | (4) Cl | H | OC₂H₅, N(CH₃)(C₂H₅) | (I-2) |
| 207 | O | CH₃ | H | (2) Cl | (4) SO₂CH₃ | H | OC₂H₅, N(CH₃)(C₂H₅) | (I-2) |
| 208 | O | C₂H₅ | H | (2) Cl | (4) SO₂CH₃ | H | OC₂H₅, N(CH₃)(C₂H₅) | (I-2) |
| 209 | O | CH₃ | CH₃ | (2) Cl | (4) SO₂CH₃ | H | OC₂H₅, N(CH₃)(C₂H₅) | (I-2) |

TABLE 1-continued

| | | | | | | | | |
|---|---|---|---|---|---|---|---|---|
| 210 | O | C$_2$H$_5$ | CH$_3$ | (2) Cl | (4) SO$_2$CH$_3$ | H | 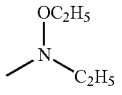 | (I-2) |
| 211 | O | C$_2$H$_5$ | H | (2) Cl | (4) SO$_2$CH$_3$ | H | 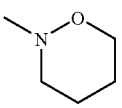 | (I-2) |
| 212 | O | CH$_3$ | H | (2) Cl | (4) SO$_2$CH$_3$ | H | 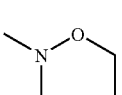 | (I-2) |
| 213 | O | C$_2$H$_5$ | CH$_3$ | (2) Cl | (4) SO$_2$CH$_3$ | H | 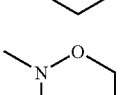 | (I-2) |
| 214 | O | CH$_3$ | CH$_3$ | (2) Cl | (4) SO$_2$CH$_3$ | H | 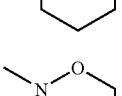 | (I-2) |
| 215 | O | CH$_3$ | H | (2) Cl | (4) Cl | H | 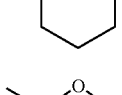 | (I-2) |
| 216 | O | C$_2$H$_5$ | CH$_3$ | (2) Cl | (4) Cl | H | 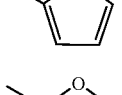 | (I-2) |
| 217 | O | CH$_3$ | CH$_3$ | (2) Cl | (4) Cl | H | 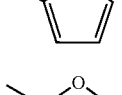 | (I-2) |
| 218 | O | C$_2$H$_5$ | H | (2) Cl | (4) SO$_2$CH$_3$ | H | 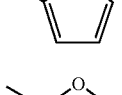 | (I-2) |
| 219 | O | CH$_3$ | H | (2) Cl | (4) SO$_2$CH$_3$ | H | 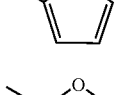 | (I-2) |
| 220 | O | C$_2$H$_5$ | CH$_3$ | (2) Cl | (4) SO$_2$CH$_3$ | H | 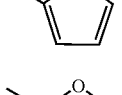 | (I-2) |
| 221 | O | CH$_3$ | CH$_3$ | (2) Cl | (4) SO$_2$CH$_3$ | H | 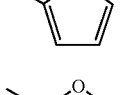 | (I-2) |
| 222 | O | C$_2$H$_5$ | H | (2) Cl | (4) SO$_2$CH$_3$ | H | 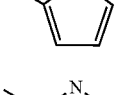 | (I-2) |
| 223 | O | CH$_3$ | H | (2) Cl | (4) SO$_2$CH$_3$ | H | 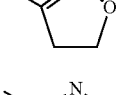 | (I-2) |
| 224 | O | C$_2$H$_5$ | CH$_3$ | (2) Cl | (4) SO$_2$CH$_3$ | H | 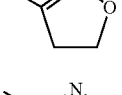 | (I-2) |

TABLE 1-continued

| 225 | O | CH₃ | CH₃ | (2) Cl | (4) SO₂CH₃ | H | 3-methylisoxazoline | (I-2) |
|---|---|---|---|---|---|---|---|---|
| 226 | O | C₂H₅ | H | (2) Cl | (4) SO₂CH₃ | H | N(OCH₃)(CH₃) | (I-2) |
| 227 | O | C₂H₅ | CH₃ | (2) Cl | (4) SO₂CH₃ | H | N(OCH₃)(CH₃) | (I-2) |
| 228 | O | CH₃ | CH₃ | (2) Cl | (4) SO₂CH₃ | H | N(OCH₃)(CH₃) | (I-2) |
| 229 | O | CH₃ | H | (2) Cl | (4) SO₂CH₃ | H | isoxazolidin-2-yl | (I-2) |
| 230 | O | C₂H₅ | H | (2) Cl | (4) SO₂CH₃ | H | isoxazolidin-2-yl | (I-2) |
| 231 | O | C₂H₅ | CH₃ | (2) Cl | (4) SO₂CH₃ | H | isoxazolidin-2-yl | (I-2) |
| 232 | O | CH₃ | CH₃ | (2) Cl | (4) SO₂CH₃ | H | isoxazolidin-2-yl | (I-2) |
| 233 | O | C₂H₅ | H | (2) Cl | (4) SO₂CH₃ | H | pyrrolidin-1-yl | (I-2) |
| 234 | O | C₂H₅ | CH₃ | (2) Cl | (4) SO₂CH₃ | H | pyrrolidin-1-yl | (I-2) |
| 235 | O | CH₃ | CH₃ | (2) Cl | (4) SO₂CH₃ | H | pyrrolidin-1-yl | (I-2) |
| 236 | O | CH₃ | H | (2) Cl | (4) SO₂CH₃ | H | piperidin-1-yl | (I-2) |
| 237 | O | C₂H₅ | H | (2) Cl | (4) SO₂CH₃ | H | piperidin-1-yl | (I-2) |
| 238 | O | C₂H₅ | CH₃ | (2) Cl | (4) SO₂CH₃ | H | piperidin-1-yl | (I-2) |

TABLE 1-continued
| 239 | O | CH₃ | CH₃ | (2) Cl | (4) SO₂CH₃ | H | 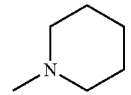 | (I-2) |
| 240 | O | C₂H₅ | H | (2) Cl | (4) SO₂CH₃ | H | 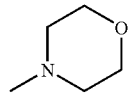 | (I-2) |
| 241 | O | C₂H₅ | CH₃ | (2) Cl | (4) SO₂CH₃ | H | 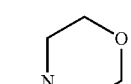 | (I-2) |
| 242 | O | CH₃ | CH₃ | (2) Cl | (4) SO₂CH₃ | H | 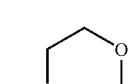 | (I-2) |
| 243 | O | CH₃ | H | (2) Cl | (4) Cl | H | 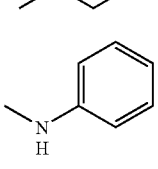 | (I-2) |
| 244 | O | C₂H₅ | H | (2) Cl | (4) Cl | H | 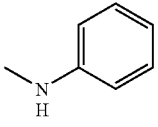 | (I-2) |
| 245 | O | CH₃ | CH₃ | (2) Cl | (4) Cl | H | 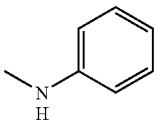 | (I-2) |
| 246 | O | C₂H₅ | CH₃ | (2) Cl | (4) Cl | H | 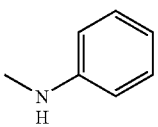 | (I-2) |
| 247 | O | CH₃ | H | (2) Cl | (4) SO₂CH₃ | H | 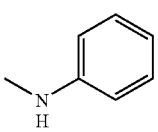 | (I-2) |
| 248 | O | C₂H₅ | H | (2) Cl | (4) SO₂CH₃ | H | 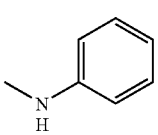 | (I-2) |
| 249 | O | CH₃ | CH₃ | (2) Cl | (4) SO₂CH₃ | H | 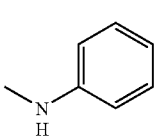 | (I-2) |
| 250 | O | C₂H₅ | CH₃ | (2) Cl | (4) SO₂CH₃ | H | 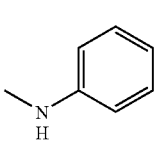 | (I-2) |

TABLE 1-continued
| 251 | O | CH₃ | H | (2) Cl | (4) Cl | H | 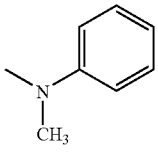 | (I-2) |
| --- | --- | --- | --- | --- | --- | --- | --- | --- |
| 252 | O | C₂H₅ | H | (2) Cl | (4) Cl | H | 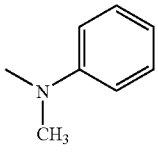 | (I-2) |
| 253 | O | CH₃ | CH₃ | (2) Cl | (4) Cl | H | 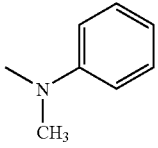 | (I-2) |
| 254 | O | C₂H₅ | CH₃ | (2) Cl | (4) Cl | H | 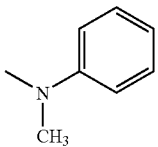 | (I-2) |
| 255 | O | CH₃ | H | (2) Cl | (4) SO₂CH₃ | H | 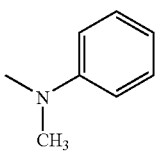 | (I-2) |
| 256 | O | C₂H₅ | H | (2) Cl | (4) SO₂CH₃ | H | 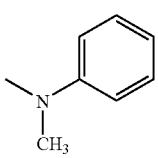 | (I-2) |
| 257 | O | CH₃ | CH₃ | (2) Cl | (4) SO₂CH₃ | H | 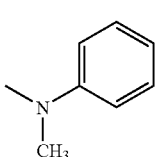 | (I-2) |
| 258 | O | C₂H₅ | CH₃ | (2) Cl | (4) SO₂CH₃ | H | 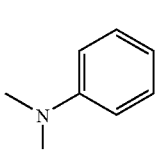 | (I-2) |
| 259 | O | CH₃ | H | (2) Cl | (4) Cl | H | 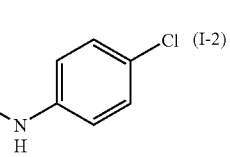 | (I-2) |
| 260 | O | C₂H₅ | H | (2) Cl | (4) Cl | H | 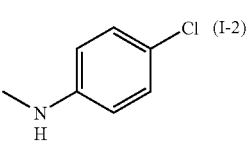 | (I-2) |

TABLE 1-continued
| 261 | O | CH₃ | CH₃ | (2) Cl | (4) Cl | H | 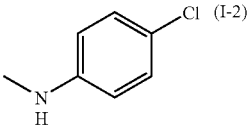 | (I-2) |
| 262 | O | C₂H₅ | CH₃ | (2) Cl | (4) Cl | H | 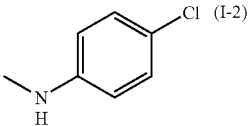 | (I-2) |
| 263 | O | CH₃ | H | (2) Cl | (4) SO₂CH₃ | H | 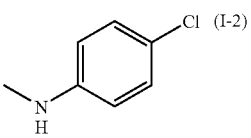 | (I-2) |
| 264 | O | C₂H₅ | H | (2) Cl | (4) SO₂CH₃ | H | 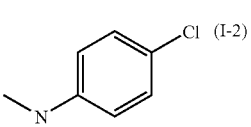 | (I-2) |
| 265 | O | CH₃ | CH₃ | (2) Cl | (4) SO₂CH₃ | H | 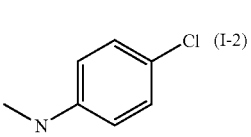 | (I-2) |
| 266 | O | C₂H₅ | CH₃ | (2) Cl | (4) SO₂CH₃ | H | 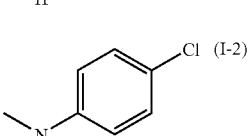 | (I-2) |
| 267 | O | CH₃ | H | (2) Cl | (4) Cl | H | 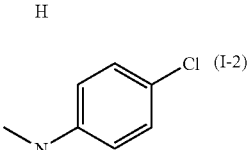 | (I-2) |
| 268 | O | C₂H₅ | H | (2) Cl | (4) Cl | H | 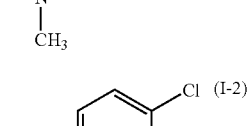 | (I-2) |
| 269 | O | CH₃ | CH₃ | (2) Cl | (4) Cl | H | 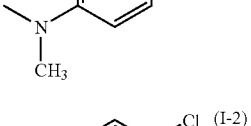 | (I-2) |
| 270 | O | C₂H₅ | CH₃ | (2) Cl | (4) Cl | H | 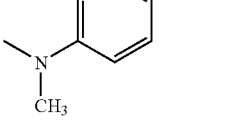 | (I-2) |

TABLE 1-continued
| 271 | O | CH₃ | H | (2) Cl | (4) SO₂CH₃ | H | 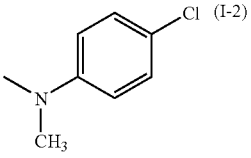 | (I-2) |
| 272 | O | C₂H₅ | H | (2) Cl | (4) SO₂CH₃ | H | 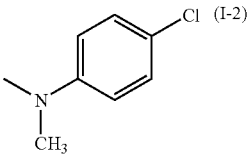 | (I-2) |
| 273 | O | CH₃ | CH₃ | (2) Cl | (4) SO₂CH₃ | H | 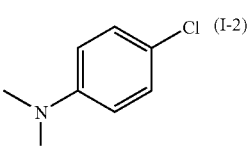 | (I-2) |
| 274 | O | C₂H₅ | CH₃ | (2) Cl | (4) SO₂CH₃ | H | 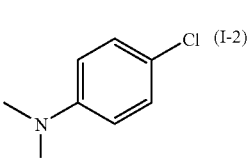 | (I-2) |
| 275 | O | CH₃ | H | (2) Cl | (4) Cl | H | 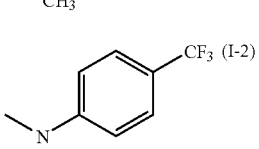 | (I-2) |
| 276 | O | C₂H₅ | H | (2) Cl | (4) Cl | H | 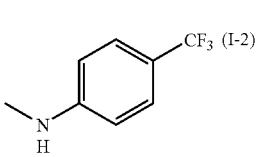 | (I-2) |
| 277 | O | CH₃ | CH₃ | (2) Cl | (4) Cl | H | 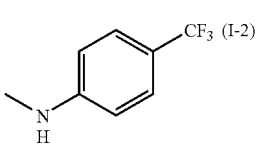 | (I-2) |
| 278 | O | C₂H₅ | CH₃ | (2) Cl | (4) Cl | H | 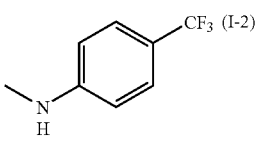 | (I-2) |
| 279 | O | CH₃ | H | (2) Cl | (4) SO₂CH₃ | H | 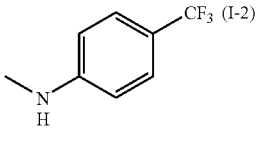 | (I-2) |
| 280 | O | C₂H₅ | H | (2) Cl | (4) SO₂CH₃ | H | 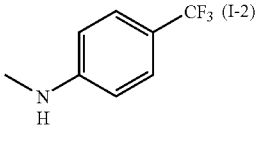 | (I-2) |

TABLE 1-continued
| | | | | | | | |
|---|---|---|---|---|---|---|---|
| 281 | O | CH₃ | CH₃ | (2) Cl | (4) SO₂CH₃ | H | 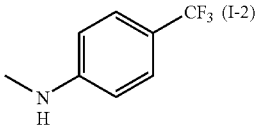 (I-2) |
| 282 | O | C₂H₅ | CH₃ | (2) Cl | (4) SO₂CH₃ | H | 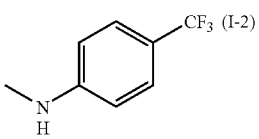 (I-2) |
| 283 | O | CH₃ | H | (2) Cl | (4) Cl | H | 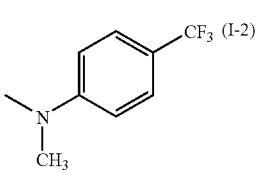 (I-2) |
| 284 | O | C₂H₅ | H | (2) Cl | (4) Cl | H | 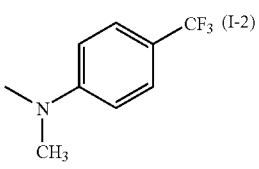 (I-2) |
| 285 | O | CH₃ | CH₃ | (2) Cl | (4) Cl | H | 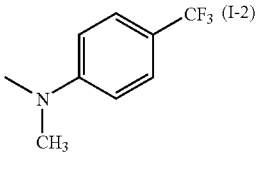 (I-2) |
| 286 | O | C₂H₅ | CH₃ | (2) Cl | (4) Cl | H | 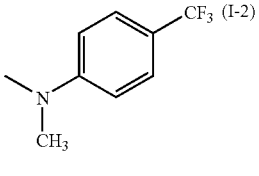 (I-2) |
| 287 | O | CH₃ | H | (2) Cl | (4) SO₂CH₃ | H | 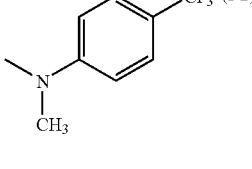 (I-2) |
| 288 | O | C₂H₅ | H | (2) Cl | (4) SO₂CH₃ | H | 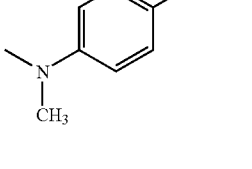 (I-2) |
| 289 | O | CH₃ | CH₃ | (2) Cl | (4) SO₂CH₃ | H | 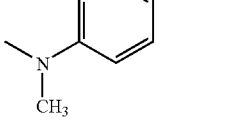 (I-2) |

TABLE 1-continued
| 290 | O | C₂H₅ | CH₃ | (2) Cl | (4) SO₂CH₃ | H | 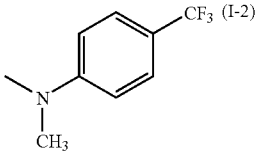 | (I-2) |
| --- | --- | --- | --- | --- | --- | --- | --- | --- |
| 291 | S | CH₃ | H | (2) Cl | (4) Cl | H | 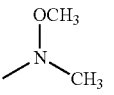 | (I-2) |
| 292 | S | C₂H₅ | H | (2) Cl | (4) Cl | H | 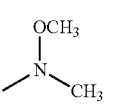 | (I-2) |
| 293 | S | CH₃ | CH₃ | (2) Cl | (4) Cl | H | 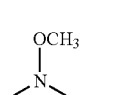 | (I-2) |
| 294 | S | C₂H₅ | CH₃ | (2) Cl | (4) Cl | H | 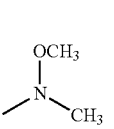 | (I-2) |
| 295 | S | CH₃ | H | (2) Cl | (4) SO₂CH₃ | H | 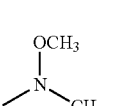 | (I-2) |
| 296 | S | C₂H₅ | H | (2) Cl | (4) SO₂CH₃ | H | 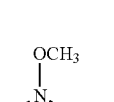 | (I-2) |
| 297 | 5 | CH₃ | CH₃ | (2) Cl | (4) SO₂CH₃ | H | 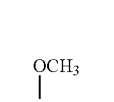 | (I-2) |
| 298 | S | C₂H₅ | CH₃ | (2) Cl | (4) SO₂CH₃ | H | 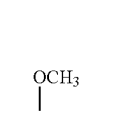 | (I-2) |
| 299 | S | CH₃ | H | (2) Cl | (4) Cl | H | 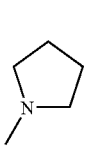 | (I-2) |

TABLE 1-continued

| | | | | | | | | |
|---|---|---|---|---|---|---|---|---|
| 300 | S | C₂H₅ | H | (2) Cl | (4) Cl | H | 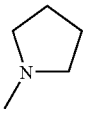 | (I-2) |
| 301 | S | CH₃ | CH₃ | (2) Cl | (4) Cl | H | 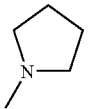 | (I-2) |
| 302 | S | C₂H₅ | CH₃ | (2) Cl | (4) Cl | H | 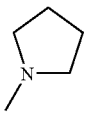 | (I-2) |
| 303 | S | CH₃ | H | (2) Cl | (4) SO₂CH₃ | H | 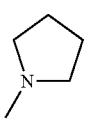 | (I-2) |
| 304 | S | C₂H₅ | H | (2) Cl | (4) SO₂CH₃ | H | 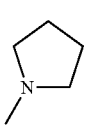 | (I-2) |
| 305 | S | CH₃ | CH₃ | (2) Cl | (4) SO₂CH₃ | H | 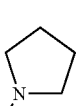 | (I-2) |
| 306 | S | C₂H₅ | CH₃ | (2) Cl | (4) SO₂CH₃ | H | 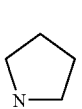 | (I-2) |

The logP valvues given Table 1 were in accordance with EEC directive 79/831 Annex V.A8 HPLC (High Performance Liquid Chromatography) using a reversed-phase column (C 18) Temperature: 43° C.

(a) Mobile phases for the determination in the acidic range: 0.1% aqueous phosphoric acid, acetonitrile; linear gradient from 10% acetonitrile to 90% acetonitrile—the corresponding measurement results in Table 1 are marked [a].

(b) Mobile phases for the determination in the neutral range: 0.01 molar aqueous phosphate buffer solution, acetonitrile; linear gradient from 10% acetonitrile to 90% acetonitrile—the corresponding measurement results in Table 1 are marked [b].

Calibration was carried out using unbranched alkan-2-ones (having 3 to 16 carbon atoms) with known logP values (determination of the logP values by the retention times using linear interpolation between two successive alkanols).

The lambda max values were determined in the maxima of the chromatographic signals using the UV spectra from 200 nm to 400 nm.

Starting Materials of the Formula (III)

Example (III-1)

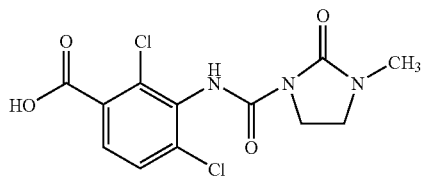

A mixture of 11.3 g (32.9 mMol) of methyl 2,4-dichloro-3-[[(3-methyl-2-oxo-1-imidazolidinyl)-carbonyl]-amino]-benzoate, 50 ml of water, 50 ml of tetrahydrofuran and 1.3 g of sodium hydroxide is stirred at room temperature (about 20° C.) for 18 hours and then concentrated under reduced pressure to about half its original volume. The mixture is then shaken with diethyl ether, the organic phase is separated off (and discarded) and the aqueous phase is acidified with conc. hydrochloric acid. The resulting crystalline product is isolated by filtration with suction.

This gives 9.1 g (81.5% of theory) of 2,4-dichloro-3-[[(3-methyl-2-oxo-1-imidazolidinyl)-carbonyl]-amino]-benzoic acid.

logP (pH=2.3): 1.35.

Analogously to Example (III-1), it is also possible to prepare, for example, the compounds of the general formula (III) listed in Table 2 below.

TABLE 2

Examples of the compounds of the formula (III) (III)

| Ex.-No. | (position) R³ | (position) R⁴ | R⁵ | Physical Data |
|---------|---------------|---------------|----|---------------|
| III-2 | (2) Cl | (4) Cl | H₃C–N–OCH₃ (with –N(H)–C(=O)–) | logP = 1.17[a] |
| III-3 | (2) Cl | (4) Cl | 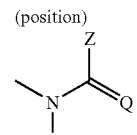 | |
| III-4 | (2) Cl | (4) Cl | 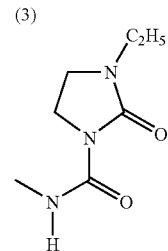 | logP = 1.58[a] |
| III-5 | (2) Cl | (4) Cl | (3) 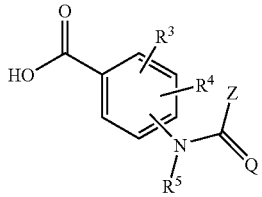 | |
| III-6 | (2) Cl | (4) Cl | (3) 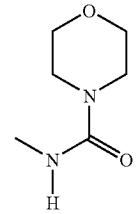 | logP = 0.78[a] |
| III-7 | (2) Cl | (4) Cl | (3) H–N–N(CH₃)₂ (with –N(H)–C(=O)–) | logP = 1.05[a] |
| III-8 | (2) Cl | (4) Cl | (3) 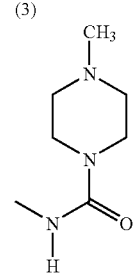 | |
| III-9 | (4) CF₃ | — | (2) H₃C–N–OCH₃ (with –N(H)–C(=O)–) 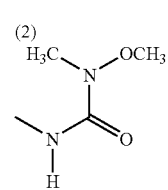 | logP = 2.43[a] |

TABLE 2-continued

Examples of the compounds of the formula (III)

| Ex.-No. | (position) R³ | (position) R⁴ | (position) R⁵ | Physical Data |
|---|---|---|---|---|
| III-10 | (4) CF₃ | — | (2) [1-methyl-imidazolidin-2-one-carbonyl-NH-CH₃] | logP = 2.13ᵃ⁾ |
| III-11 | (4) CF₃ | — | (2) [1-methyl-tetrahydropyrimidin-2-one-carbonyl-NH-CH₃] | |
| III-12 | (4) CF₃ | — | (2) [1-ethyl-imidazolidin-2-one-carbonyl-NH-CH₃] | |
| III-13 | (4) CF₃ | — | (2) [morpholine-carbonyl-NH-CH₃] | |
| III-14 | (4) CF₃ | — | (2) [N(CH₃)₂-NH-carbonyl-NH-CH₃] | |
| III-15 | (4) CF₃ | — | (2) [4-methyl-piperazine-carbonyl-NH-CH₃] | |

Starting Materials of the Formula (IIIa)

Example (IIIa-1)

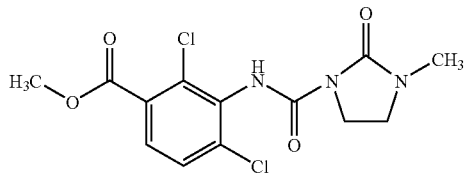

A mixture of 12.3 g (50 mMol) of methyl 2,4-dichloro-3-isocyanato-benzoate, 5.0 g (50 mmol) of 1-methyl-2-oxo-imidazolidine, a few drops of triethylamine and 100 ml of acetonitrile is stirred at room temperature (about 20° C.) for 18 hours and then concentrated under reduced pressure. The residue is then digested with diethyl ether and the crystalline product is isolated by filtration with suction.

This gives 11.4 g (60% of theory) of methyl 2,4-dichloro-3-[[(3-methyl-2-oxo-1-imidazolidinyl)-carbonyl]-amino]-benzoate.

logP (pH=2.3): 1.94.

Analogously to Example (IIIa-1) it is also possible to prepare, for example, the compounds of the general formula (IIIa) listed in Table 3 below.

TABLE 3
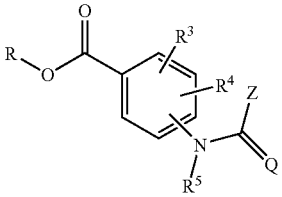
Examples of the compounds of the formula (IIIa)
| Ex.-No. | R | (position) R³ | (position) R⁴ | (position) 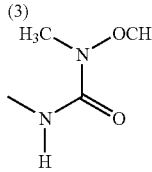 | Physical Data |
|---|---|---|---|---|---|
| IIIa-2 | CH₃ | (2) Cl | (4) Cl | (3) 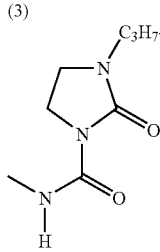 | |
| IIIa-3 | CH₃ | (2) Cl | (4) Cl | (3) 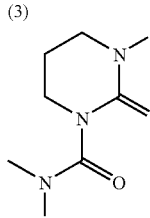 | |
| IIIa-4 | CH₃ | (2) Cl | (4) Cl | (3) 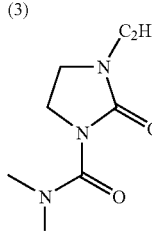 | |
| IIIa-5 | CH₃ | (2) Cl | (4) Cl | (3)  | |

TABLE 3-continued

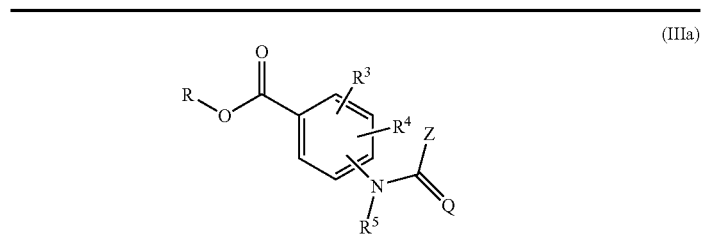

Examples of the compounds of the formula (IIIa)

| Ex.-No. | R | (position) R³ | (position) R⁴ | (position) Z–C(=Q)–N(R⁵)– | Physical Data |
|---|---|---|---|---|---|
| IIIa-6 | CH₃ | (2) Cl | (4) Cl | (3) N-methylcarbamoyl-morpholine | logP = 1.34[a] |
| IIIa-7 | CH₃ | (2) Cl | (4) Cl | (3) N-methylcarbamoyl-N'-H-N''-N(CH₃)₂ hydrazide | logP = 1.64[a] |
| IIIa-8 | CH₃ | (2) Cl | (4) Cl | (3) N-methylcarbamoyl-4-methylpiperazine | logP = 0.50[a] |
| IIIa-9 | CH₃ | (4) CF₃ | — | (2) N-methylcarbamoyl-N(CH₃)(OCH₃) | logP = 3.35[a] |
| IIIa-10 | CH₃ | (4) CF₃ | — | (2) N-methylcarbamoyl-3-methyl-2-oxoimidazolidine | logP = 2.76[a] |

TABLE 3-continued
Examples of the compounds of the formula (IIIa)
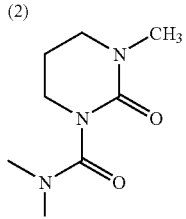
| Ex.-No. | R | (position) R³ | (position) R⁴ | (position) $\underset{R^5}{\overset{Z}{\underset{|}{N}}}\!\!\!\overset{}{\underset{Q}{\overset{}{\diagdown}}}$ | Physical Data |
|---|---|---|---|---|---|
| IIIa-11 | CH₃ | (4) CF₃ | — | (2) 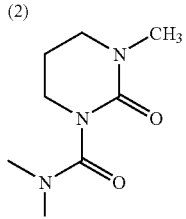 | |
| IIIa-12 | CH₃ | (4) CF₃ | — | (2) 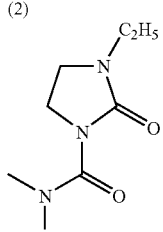 | |
| IIIa-13 | CH₃ | (4) CF₃ | — | (2) 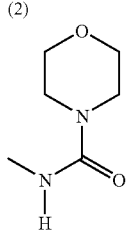 | |
| IIIa-14 | CH₃ | (4) CF₃ | — | (2) 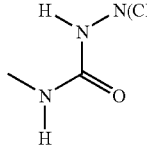 | |

TABLE 3-continued (IIIa)

Examples of the compounds of the formula (IIIa)

| Ex.-No. | R | (position) R³ | (position) R⁴ | (position) Z–C(=O)–Q on N–R⁵ | Physical Data |
|---|---|---|---|---|---|
| IIIa-15 | CH₃ | (4) CF₃ | — | (2) R⁵=CH₃; Q = N-methylpiperazine-N'-yl; Z = NH | |
| IIIa-16 | CH₃ | (2) Cl | (4) Cl | (3) R⁵=CH₃; Q = 4-methyl-5-methylthio-3-oxo-1-methyl-1,2,4-triazol-2-yl | |

Use Examples

Example A

Pre-emergence Test

| Solvent: | 5 parts by weight of acetone |
|---|---|
| Emulsifier: | 1 part by weight of alkylarylpolyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Examples 1, 2, 3, 4, 5 and 6 exhibit strong activity against weeds, and some are tolerated well by crop plants, such as, for example, maize.

Example B

Post-emergence Test

| Solvent: | 5 parts by weight of acetone |
|---|---|
| Emulsifier: | 1 by weight of alkylarylpolyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction In this test, for example, the compounds of Preparation Examples 1, 2, and 5 exhibit strong activity against weeds.

What is claimed is:

1. A compound of formula (I)

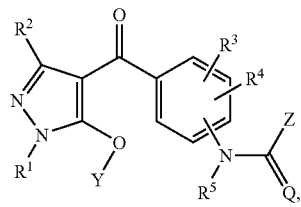

including any tautomeric forms thereof or a salt of a compound of formula (I) including any tautomeric forms thereof, in which Q represents O (oxygen) or S (sulphur), $R^1$ represents methyl, ethyl, or n- or i-propyl, $R^2$ represents hydrogen, methyl, ethyl, methoxycarbonyl, ethoxycarbonyl, methylthio, or ethylthio, $R^3$ and $R^4$ independently of one another represent hydrogen, nitro, cyano, fluorine, chlorine, bromine, methyl, ethyl, difluoromethyl, trifluoromethyl, dichloro-methyl, trichloromethyl, methoxymethyl, methylthiomethyl, methylsulphinyl-methyl, methylsulphonylmethyl, methoxy, ethoxy, difluoromethoxy, trifluoro-methoxy, methylthio, ethylthio, methylsulphinyl, ethylsulphinyl, methyl-sulphonyl, ethylsulphonyl, or dimethylaminosulphonyl, $R^5$ represents hydrogen; represents methyl, ethyl, or n- or i-propyl; represents methylthio, ethylthio, n- or i-propylthio, methylsulphinyl, ethylsulphinyl, n- or i-propylsulphinyl, methylsulphonyl, or ethylsulphonyl; represents optionally fluorine- and/or chlorine-substituted propenyl, butenyl, propynyl, or butynyl; or represents cyclopropyl, Y represents hydrogen; represents optionally cyano-, fluorine-, methoxy-, ethoxy-, methoxycarbonyl-, or ethoxycarbonyl-substituted methyl or ethyl; represents optionally fluorine- and/or chlorine-substituted methylsulphonyl or ethylsuiphonyl; represents optionally cyano-, fluorine-, chlorine-, methoxy-, or ethoxy-substituted acetyl, propionyl, methoxycarbonyl, ethoxycarbonyl, methylaminocarbonyl, or ethylaminocarbonyl; represents dimethylamino-carbonyl; represents optionally fluorine-, chlorine-, or bromine-substituted propenyl, propenylcarbonyl, propynyl, or propynylcarbonyl; represents optionally cyano-, fluorine-, chlorine- or methyl-substituted cyclopropyl-carbonyl, cyclobutylcarbonyl, cyclopentylcarbonyl, cyclohexylcarbonyl, cyclopropylmethyl, cyclobutylmethyl, cyclopentylmethyl, or cyclohexylmethyl; or represents optionally nitro-, cyano-, fluorine-, chlorine-, bromine-, methyl-, ethyl-, trifluoromethyl-, methoxy-, ethoxy-, difluoromethoxy-, or trifluoro-methoxy-substituted phenyl, phenylsulphonyl, phenylcarbonyl, phenylmethyl, phenylmethylsulphonyl, phenylmethylcarbonyl, or phenylcarbonylmethyl and Z represents cyanoamino, or hydrazino; represents methoxyamino, ethoxyamino, n- or i-propoxyamino, methylhydrazino, ethylhydrazino, n- or i-propylhydrazino, or n-, i-, s-, or t-butylhydrazino; represents N-methyl-methoxyamino or dimethylhydrazino; represents optionally fluorine- and/or chlorine-substituted propenyloxy, butenyloxy, propenylthio, butenylthio, propenylamino, butenylamino, propenyloxyamino, butenyloxyamino, propynyloxy, butynyloxy, propynylamino, or butynylamino; represents optionally cyano-, fluorine-, chlorine- or methyl-substituted cyclopropyl, cyclopentyl, cyclohexyl, cyclopropyloxy, cyclopentyloxy, cyclohexyloxy, cyclopropylamino, cyclopentylamino, cyclohexylamino, cyclohexylhydrazino, cyclopropylmethoxy, cyclopentylmethoxy, cyclohexylmethoxy, cyclopropyl-methylamino, cyclopentylmethylamino, or cyclohexylmethylamino; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methoxycarbonyl-, ethoxy-carbonyl-, or n- or i-propoxycarbonyl-substituted phenyl, phenylcarbonyl, phenoxy, phenoxycarbonyl, phenylthio, phenylamino, phenylhydrazino, phenylmethoxy, phenylethoxy, phenylmethylthio, phenylethylthio, phenylmethylamino, or phenylethylamino; or represents optionally nitro-, cyano-, fluorine-, chlorine-, bromine-, methyl-, ethyl-, n- or i-propyl-, n-, i-, s-, or t-butyl-, cyclopropyl-, cyclobutyl-, cyclopentyl-, cyclohexyl-, difluoromethyl-, trifluoromethyl-, dichloromethyl-, trichloromethyl-, chlorodifluoromethyl-, fluorodichioromethyl-, methoxy-, ethoxy-, n- or i-propoxy-, difluoromethoxy-, trifluoromethoxy-, methylthio-, ethylthio-, n- or i-propylthio-, difluoromethyl-thio-, trifluoromethyithio-, methoxycarbonyl-, ethoxycarbonyl-, or n- or i-propoxycarbonyl-substituted monocyclic or bicyclic heterocyclyl, heterocyclyl-oxy, heterocyclylamino, heterocyclylalkyl, heterocyclylalkoxy, or heterocyclyl-alkylamino selected from the group consisting of furyl, furyloxy, furylamino, furylmethoxy, furylmethylamino, tetrahydrofuryl, tetrahydrofuryloxy, tetrahydrofurylamino, tetrahydrofurylmethoxy, tetrahydrofurylmethylamino, dioxolanyl, dioxolanylmethoxy, dioxolanylmethylamino, thienyl, thienylamino, thienylmethylamino, dithiolanyl, dithiolanylmethoxy, dithiolanylmethylamino, pyrrolidinyl, pyrrolidinylamino, oxopyrrolidinyl, pyrrolyl, indolyl, pyrazolyl, pyrazolyloxy, pyrazolylamino, imidazolyl, imidazolinyl, 2-oxo-1,3-diaza-cyclopentyl, oxazolyl, oxazolylmethyl, dihydrooxazolyl (oxazolinyl), tetrahydro-oxazolyl (oxazolidinyl), isoxazolyl, dihydroisoxazolyl (isoxazolinyl), tetrahydro-isoxazolyl (isoxazolidinyl), thiazolyl, dihydrothiazolyl (thiazolinyl), tetrahydro-thiazolyl (thiazolidinyl), oxothiazolidinyl, cyanoiminothiazolidinyl, oxotriazolinyl, oxotetrazolinyl, dioxanyl, dioxanylmethoxy, dioxanylmethylamino, dithianyl, dithianylmethoxy, dithianylmethylamino, triazolylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, oxomorpholinyl, morpholinylamino, piperazinyl, pyridinyl, pyridinyloxy, pyridinylamino, pyridinylmethoxy, pyrimidinyl, pyrimidinyloxy, and pyrimidinylmethoxy.

2. A process for preparing a compound of formula (I) according to claim 1 comprising
(a) reacting a pyrazole of formula (II)

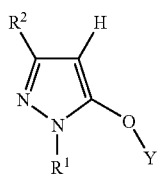
(II)

in which $R^1$, $R^2$, and Y are as defined for formula (I) in claim 1, with a substituted benzoic acid of formula (III)

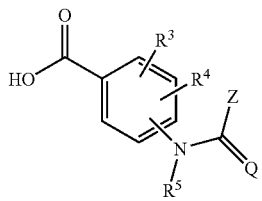
(III)

in which Q, $R^3$, $R^4$, $R^5$ and Z are as defined for formula (I) in claim 1, or a reactive derivative thereof,
optionally in the presence of a dehydrating agent, optionally in the presence of one or more reaction auxiliaries, and optionally in the presence of one or more diluents,
or
(b) reacting a substituted benzoylpyrazole of formula (Ia)

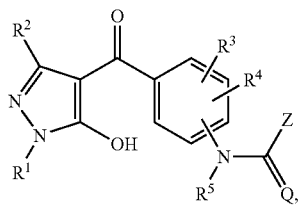
(Ia)

in which Q, $R^1$, $R^2$, $R^3$, $R^4$, $R^5$ and Z are as defined for formula (I) in claim 1,
with a compound of formula (IV)

X—Y     (IV)

in which
Y is as defined for formula (I) in claim 1, except for excluding hydrogen, and
X represents halogen,
or optionally with a corresponding acid anhydride, isocyanate, or isothiocyanate,
optionally in the presence of one or more reaction auxiliaries and optionally in the presence of one or more diluents.

3. A process according to claim 2 additionally comprising (i) subjecting the resulting compound of formula (I) to electrophilic or nucleophilic substitution reactions and/or oxidation or reduction reactions to interconvert substituents within the meaning of formula (I) and/or (ii) converting the resulting compound of formula (I) into a salt thereof.

4. A herbicidal composition comprising one or more compounds of formula (I) according to claim 1 and one or more extenders.

5. A method for controlling undesirable plants comprising allowing one or more compounds according to claim 1 to act on an undesirable plant and/or its habitat.

6. A compound of formula (I-a)

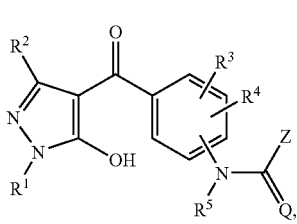
(I-a)

in which
Q represents O (oxygen) or S (sulphur),
$R^1$ represents optionally substituted alkyl, alkenyl, alkynyl, or cycloalkyl,
$R^2$ represents hydrogen, cyano, carbamoyl, thiocarbamoyl, or halogen; or represents optionally substituted alkyl, alkoxy, alkylthio, alkoxycarbonyl, or cycloalkyl,
$R^3$ and $R^4$ independently of one another represent hydrogen, nitro, cyano, carboxyl, carbamoyl, thiocarbamoyl, halogen, or optionally substituted alkyl, alkoxy, alkylthio, alkylsulphinyl, alkylsulphonyl, alkylamino, dialkylamino, dialkyl-aminocarbonyl, or dialkylaminosulphonyl,
$R^5$ represents hydrogen; represents optionally substituted alkyl, alkoxy, alkylthio, alkylsulphinyl, alkylsulphonyl, alkenyl, alkynyl, cycloalkyl, cycloalkylalkyl, aryl, arylthio, arylsulphinyl, arylsulphonyl, or arylalkyl; or represents the group —C(Q)-Z, and
Z represents cyanoamino, nitroamino, hydroxyamino, or hydrazino; represents alkylthio; or represents optionally substituted alkylcarbonyl, alkoxycarbonyl, alkoxyamino, alkylhydrazino, alkylcarbonyl -hydrazino, alkoxycarbonylhydrazino, alkylsulphonylhydrazino, N-alkyl -alkoxyamino, dialkylhydrazino, alkenyloxy, alkenylamino, alkenyloxyamino, alkynyloxy, alkynylamino, cycloalkyl, cycloalkyloxy, cycloalkylamino, cycloalkylhydrazino, cycloalkylalkoxy, cycloalkylalkylamino, aryl, arylcarbonyl, aryloxy, aryloxycarbonyl, arylthio, arylamino, arylhydrazino, arylalkyl, arylalkoxy, arylalkylthio, arylalkylamino, heterocyclyl, heterocyclyloxy, heterocyclylthio, heterocyclylamino, the group —N=(heterocyclyl), heterocyclylalkoxy, heterocyclylalkylthia, or heterocyclylalkylamino.

7. A method for controlling undesirable plants comprising allowing one or more compositions according to claim 4 to act on an undesirable plant and/or its habitat.

8. A compound of the formula (I-2)

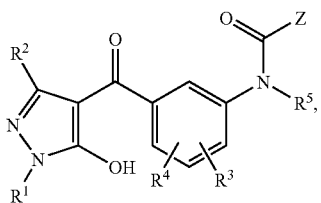

in which
Q represents O (oxygen),
$R^1$ represents optionally substituted alkyl,
$R^2$ represents hydrogen,
$R^3$ and $R^4$ independently of one another represent halogen,
$R^5$ represents hydrogen, and
Z represents alkoxy-substituted alkylamino; or represents optionally methyl-, ethyl-, n- or i-propyl, or n-, i-, s- or t-butyl-substituted heterocyclyl selected from the group consisting of pyrrolidinyl, pyrrolidinyl-amino, oxopyrrolidinyl, pyrrolyl, imidazolinyl, 2-oxo-1,3-diazacyclopentyl, dihydrooxazolyl (oxazolinyl), tetrahydrooxazolyl (oxazolidinyl), dihydro-isoxazolyl (isoxazolinyl), tetrahydroisoxazolyl (isoxazolidinyl), tetrahydro-(2H)-1,2-oxazin-2-yl, piperidinyl, oxopiperidinyl, 2-oxo-1,3-diaza-cyclohexyl, 2-oxo-1-aza-cycloheptyl, 2-oxo-1,3-diaza-cycloheptyl, morpholinyl, oxomorpholinyl, or piperazinyl.

* * * * *

UNITED STATES PATENT AND TRADEMARK OFFICE
CERTIFICATE OF CORRECTION

| | |
|---|---|
| PATENT NO. | : 7,635,664 B2 |
| APPLICATION NO. | : 10/477800 |
| DATED | : December 22, 2009 |
| INVENTOR(S) | : Schwarz et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this

Ninth Day of November, 2010

David J. Kappos
*Director of the United States Patent and Trademark Office*